United States Patent [19]

Wolfe

[11] 4,013,653
[45] Mar. 22, 1977

[54] 1-OXACEPHEMS
[75] Inventor: Saul Wolfe, Kingston, Canada
[73] Assignee: Queen's University at Kingston, Kingston, Canada
[22] Filed: July 21, 1975
[21] Appl. No.: 597,128
[30] Foreign Application Priority Data
June 30, 1975 United Kingdom ............ 34614/75
[52] U.S. Cl. .......................................... 260/244 R
[51] Int. Cl.$^2$ ............ C07D 265/00; C07D 273/00; C07D 295/00
[58] Field of Search .................................. 260/244

[56] References Cited
FOREIGN PATENTS OR APPLICATIONS
1,914,366  1/1970  Germany ........................... 260/244

Primary Examiner—Albert T. Meyers
Assistant Examiner—D. W. Robinson
Attorney, Agent, or Firm—Behr & Woodbridge

[57] ABSTRACT

The present invention relates to novel 1-oxacephems of the formula

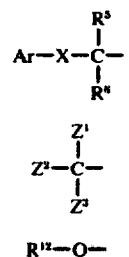

wherein $R^9$ is hydrogen and $R^8$ is hydrogen or

RCOwherein R is selected from the group consisting of lower alkyl

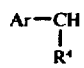

-continued

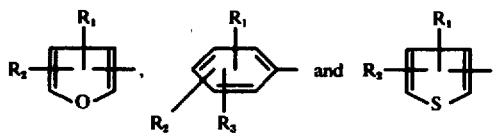

wherein Ar is a monovalent radical selected from the group consisting of

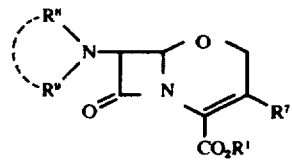

wherein
$R_1$, $R_2$ and $R_3$ are each a member selected from the group consisting of hydrogen, chloro, bromo, iodo, trifluoromethyl, phenyl, lower-alkyl and lower alkoxy, but only one of said $R_1$, $R_2$ and $R_3$ may represent phenyl;
$R^4$ is hydrogen, amino, carbobenzoxyamino, phenyl, fluoro, chloro, bromo, iodo, carboxyl, $SO_3H$, azido, hydroxy, loweralkanoyloxy or loweralkoxy;
X is oxygen or sulfur;
$R^5$ and $R^6$ are hydrogen, phenyl, benzyl, phenethyl or loweralkyl;
$Z^1$, $Z^2$ and $Z^3$ are loweralkyl or the Ar- group;
$R^{12}$ is 2,2,2-trichloroethyl or benzyl;
provided that when $R^8$ and $R^9$ are taken together with the nitrogen to which they are attached, they form a phthalimido moiety;
$R^7$ is methyl or hydroxy; and
$R^1$ is hydrogen, loweralkyl, benzyl, benzhydryl, loweralkoxyloweralkyl, loweralkoxybenzyl, phenacyl, trimethylsilyl, 2,2,2-trichloroethyl, or pivaloyloxy.

9 Claims, No Drawings

1-OXACEPHEMS

The present invention relates to a novel group of compounds which are broadly referred to as 1-oxacephems and which corresponds to the following general formula:

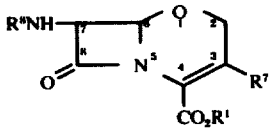

XII wherein R⁸ is hydrogen or

RCOwherein R stands for loweralkyl

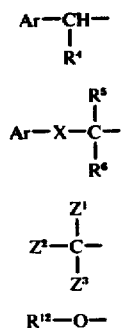

wherein Ar is a monovalent radical selected from

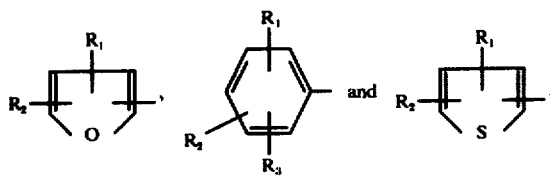

wherein
$R_1$, $R_2$ and $R_3$ are each a member selected from hydrogen, chloro, bromo, iodo, trifluoromethyl, phenyl, loweralkyl and loweralkoxy, but only one of said $R_1$, $R_2$ and $R_3$ may represent phenyl;
$R^4$ is hydrogen, amino, carbobenzoxyamino, phenyl, fluoro, chloro, bromo, iodo, carboxyl, $SO_3H$ and azido, hydroxy, loweralkanoyloxy and loweralkoxy;
X is oxygen or sulfur;
$R^5$ and $R^6$ are hydrogen, phenyl, benzyl, phenethyl and loweralkyl;
$Z^1$, $Z^2$ and $Z^3$ stand or loweralkyl or the Ar- group;
$R^{12}$ is 2,2,2-trichloroethyl or benzyl;
and the group $R^8NH$ is phthalimido;
$R^7$ is methyl or hydroxyl; and
$R^1$ is hydrogen, loweralkyl, benzyl, benzhydryl, loweralkoxyloweralkyl, loweralkoxybenzyl, phenacyl, trimethylsilyl, 2,2,2-trichloroethyl, or pivaloyloxy.

The present invention also relates to novel intermediates and to novel processes for the preparation thereof.

Also included within the scope of the present invention are the pharmaceutically acceptable salts of the above 1-oxacephems XII. The 1-oxacephems XII in either their free acid, salt, or ester form have been found to possess antibacterial activity.

Illustrative of the compounds of the present invention are the 3-methyl-4-methoxycarbonyl-7S-phthalimido-1-oxa,5-aza-6S-bicyclo[4,2,0]oct-3-en-8one; 3-methyl-4-benzhydryloxycarbonyl-7S-phthalimido-1-oxa,5-aza-bicyclo-[4,2,0]oct-3-en-8-one; 3-methyl-4-benzhydryloxycarbonyl-7S-trichloroethoxycarbonylamino-1-oxa, 5-aza-bicyclo[4,-2,0]oct-3-en-8-one, 3-methyl-4-carboxy-7S-amino-1-oxa,5-aza-6-R-bicyclo[4,2,0]oct-3-en-8-one, 3-hydroxy-4-carboxyl-7S-amino-1-oxa,5-aza-6-R-bicyclo[4,2,0]oct-3-en-8-one.

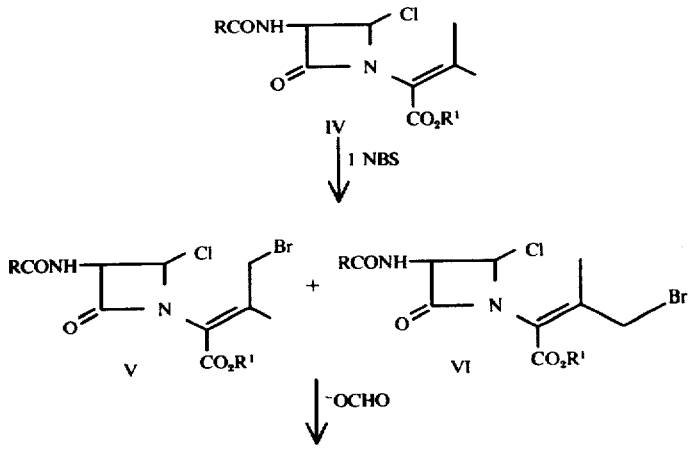

FLOWSHEET 1

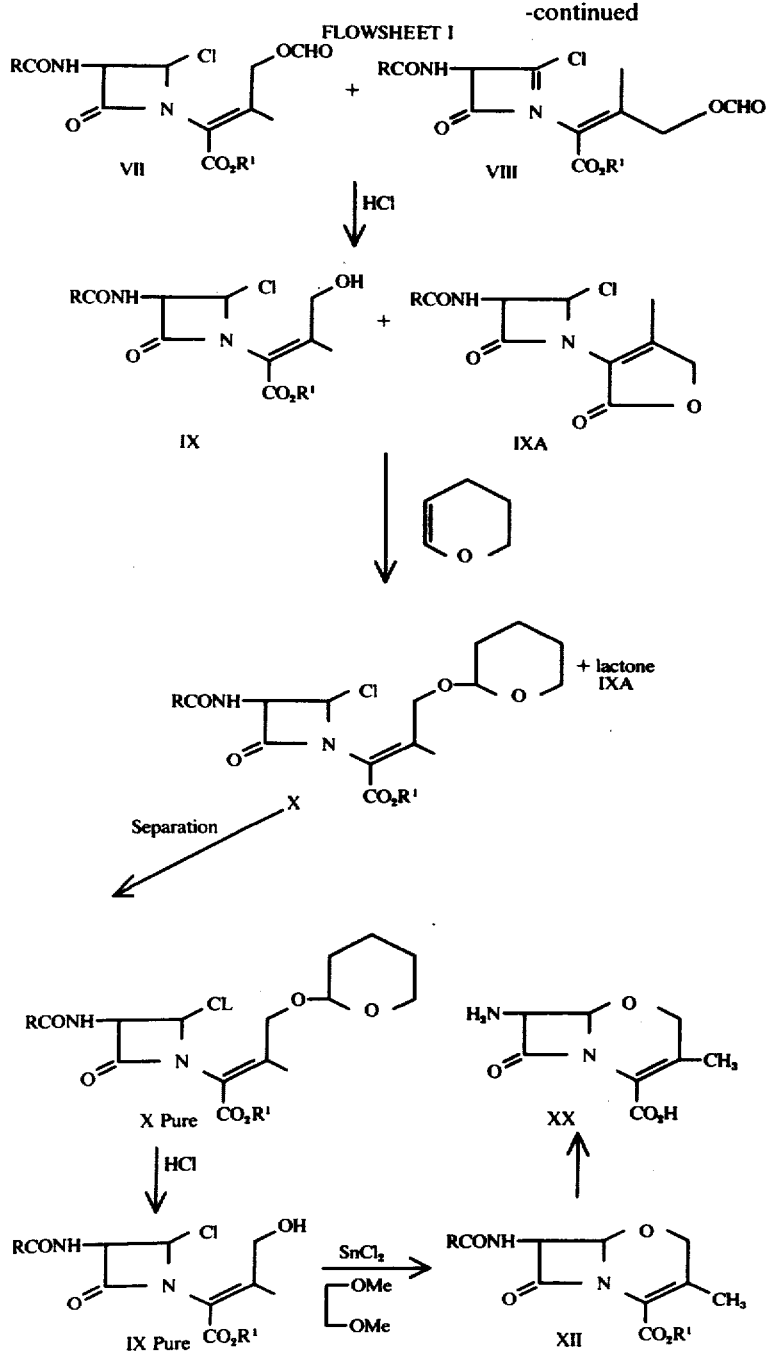

FLOWSHEET I

Referring to the above reaction sequence the starting azetidinone IV is obtained in accordance with procedures described in copending U.S. application Ser. No. 587,571 filed June 17, 1975.

The chloro azetidinone IV is brominated with N-bromosuccinimide in refluxing methylene chloride thus yielding a mixture of $R^1$ 2-(2'-chloro-3'-$\underline{S}$-R-carboxamido-4'-oxo)-azetidinyl-trans-3-bromomethyl-2-butenoate V and $R^1$ 2-(2'-chloro-3'-$\underline{S}$-R-carboxamido-4'-oxo)azetidinyl-cis-3-bromomethyl-2-butenoate VI. Preferably the N-bromosuccinimide is used in an amount of 1 molar equivalent.

The mixture of the azetidinone compounds V and VI thus obtained is then formylated with tetramethylguanidinium formate in the presence of an halogenated solvent at room temperature to provide the corresponding $R^1$ 2-(2'-chloro-3'-$\underline{S}$-R-carboxamido-4'-oxo)azetidinyl-trans-3-formyloxymethyl-2-butenoate VII and $R^1$ 2-(2'-chloro-3'$\underline{S}$-R-carboxamido-4'-oxo)-azetidinyl-cis-3-formuloxymethyl-2-butenoate VIII. The tetramethylguanidinium formate is preferably used in an amount of 5 molar equivalents The mixture of the azetidinone compounds VII and VIII thus obtained yields, upon treatment with methanolic hydrochloric acid at 0° C, a further mixture made up of $R^1$ 2-(2'-chloro-3'$\underline{S}$-R-carboxamido-4'-oxo)azetidinyl-trans-3-hydroxymethyl-2-butenoate IX and 2-oxo-2,5-dihydro-3-(2'-chloro-3'$\underline{S}$-R-carboxamido-4'-oxo)azetidinyl-4-methylfuran IXA.

In order to separate the new hydroxy azetidinone derivative IX from the chloro lactone IXA, the mixture of the two compounds is treated with dihydropyran in the presence of a catalytic amount of a sulfonic acid such as p-toluenesulfonic acid or benzensulfonic acid. In this reaction the chlorolactone IXA is unchanged while the chloro azetidinone derivative IX is converted to the corresponding novel tetrahydropyranyloxymethyl derivative which is the R$^1$ 2-(2'-chloro-3'$\underline{S}$-R-carboxamido-4'-oxo)azetidinyl-trans-3-(1-tetrahydropyranyloxymethyl)-2-butenoate X.

Separation of the ether X from the chlorolactone IXA is effected by chromatography on silica gel thereby yielding desired intermediate R$^1$ 2-(2'-chloro-3'$\underline{S}$-R-carboxamido-4'-oxo)azetidinyl-trans-3-(1-tetrahydropyrayloxymethyl)-2-butenoate (X) which is to be found in fractions 1–7.

Treatment of the novel R$^1$ 2-(2'-chloro-3'$\underline{S}$-R-carboxamido-4'-oxo)azetidinyl-trans-3-(1-tetrahydropyranyloxymethyl)-2-butenoate X with a methanolic hydrochloric acid solution provides the new R$^1$ 2-(2'-chloro-3'$\underline{S}$-R-carboxamido-4'-oxo)azetidinyl-trans-3-hydroxymethyl-2-butenoate IX obtained previously in admixture with the lactone IXA.

Also in accordance with the present invention, cyclization of the new R$^1$ yl-2-(2'-chloro-3'$\underline{S}$-R-carboxamido-4'-oxo)azetidinyl-trans-3-hydroxymethyl-2-butenoate is carried out with a Lewis acid in the presence of a solvent such as dimethoxyethane to provide the 1-oxacephem of the present invention which is the 3-methyl-4-R$^1$ oxycarbonyl-7$\underline{S}$-R-carboxyamido-1-oxa,5-azabicyclo[4,2,0]oct-3-en-8-one XII. As Lewis acids there may be used preferably stannous chloride but other acids known as Lewis acids may also be used conveniently.

The desired oxacephems XII can also be obtained by dissolving the R$^1$ 2-(2'-chloro-3'$\underline{S}$-R-carboxamido-4'-oxo)azetidinyl-trans-hydroxymethyl-2-butenoate IX in an amine base such as preferably pyridine which has a pK$_a$ of 5.2 or an amine base of equal or lesser basicity where cyclization to the oxacephem XIX occurs. When the azetidinyl compound IX has the 2'S stereochemistry, the cyclization to the oxacephem XII affords the desired cis stereochemistry of the β-lactam proton.

If desired, the oxacephem XII which is the 3-methyl-4-R$^1$-oxycarbonyl-7$\underline{S}$-R-carbonylamino-1-oxa,5-aza-6-R-bicyclo [4,2,O]oct-3-en-8-one can be readily converted to the most useful intermediate free amino derivative XX which is the 3-methyl-4-carboxy-7$\underline{S}$-amino-1-oxa,5-aza-6-$\underline{R}$-bicyclo[4,2,0]oct-3-en-8-one by removal of the RCO-radical and the R$^1$ substituent. The free amino compound XX (1-oxadethia-7-ADCA) is a most useful intermediate in the synthesis of any desired oxacephem derivative.

It is also a feature of the present invention that the critical and novel intermediate R$^1$ 2-(2'-chloro-3'$\underline{S}$-R-carboxamido-4'-oxo)azetidinyl-trans-3-methyl-4-hydroxy-2-butenoate IX obtained herein can also be derived from a different reaction scheme which involves the preparation of the novel R$^1$2-(2'-chloro-3'$\underline{S}$-R-carboxamido-4'-oxo)azetidinyl-3-methyl-3-butenoate oxide XVII corresponding to the general formula:

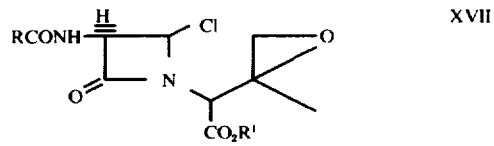

wherein R and R$^1$ are as previously defined

The reaction sequence for the preparation of the oxide XVII and its conversion to the azetidinone IX is illustrated in the following Flowsheet II:

FLOWSHEET II

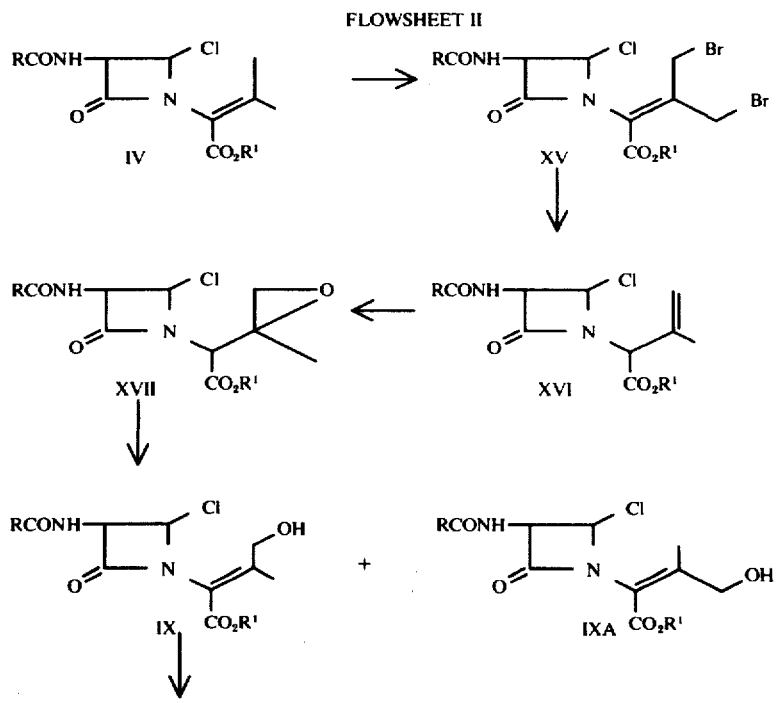

FLOWSHEET II -continued

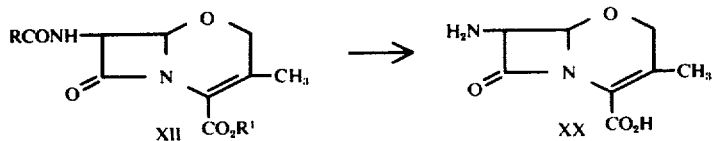

First, the chloro azetidinone IV is brominated in accordance with the procedure described in British Application Ser. No. 16642/73 filed Apr. 6, 1973 to provide the correponding dibromo azetidinone XV. Debromination with from 2 to 4 molar equivalents of zinc in a loweralkanoic acid or in a mixture of loweralkanoic acid and acetonitrile below room temperature and for a short period of time, preferably less than five minutes, provides the azetidinone XVI.

It should be appreciated that the reaction conditions for this debromination step are very critical. For example, if the debromination step is carried out for more than five minutes, instead of the 2'-chloro derivative XVI there will be obtained the 2'$\underline{S}$-acetoxy derivative XVIA of the formula:

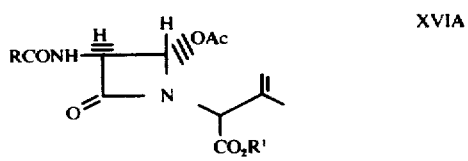

On the other hand if less than two molar equivalents of zinc are used in the debromination step there will be obtained a mixture of compounds, one of which will be the desired debrominated compound XVI while the two others will each correspond to the following structures:

Compounds XVIB and XVIC which are the $R^1$ 2R- and 2$\underline{S}$-2-(2'-chloro-3'$\underline{S}$-R-carboxamido-4'-oxo)azetidinyl-3-bromomethyl-3-butenoates are useful intermediates for the preparation of 1-oxacephems wherein there is a substituted methyl radical or electronegative atom in position 3 rather than a methyl substituent.

The novel debrominated azetidinone XVI will readily yield the desired novel azetidinone oxide XVII by treatment with a peroxy acid in a halogenated solvent at room temperature and in the presence of a buffering agent. As an example of suitable peroxy acids there may be mentioned peroxytrifluoroacetic acid or peroxymethachlorobenzoic acid and the like. As halogenated solvent there may be mentioned methylene chloride or trichloroethylene. The buffering agent is used to maintain the reaction medium slightly acidic.

The novel $R^1$ 2-(2'-chloro-3'$\underline{S}$-R-carboxamido-4'-oxo)-azetidinyl-3-methyl-2-butenoate oxide XVII may now be converted to the critical intermediate IX. In fact treating the oxide XVII with an organic nitrogen base such as di- or triethylamine in a loweralkanol solvent at 0° C will provide aa mixture of $R^1$ 2-(2'-chloro-3'$\underline{S}$-R-carboxamido-4'-oxo)azetidinyl-3-methyl-4-hydroxy-trans-2-butenoate IX and 2-oxo-2,5-dihydro-3-(2'-chloro-3'$\underline{S}$-R-carboxamido-4'-oxo)azetidinyl-4-methylfuran IXA, each corresponding to the following structures:

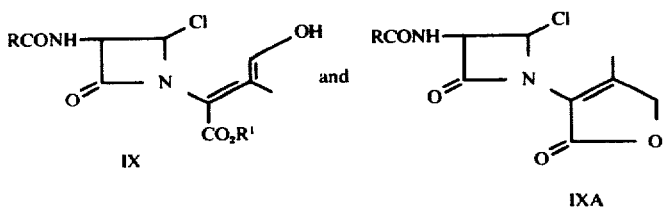

When it is desired to prepare the novel oxacephem derivatives XII where $R^1$ is hydroxy, reference should be made to Flowsheet III.

tures:

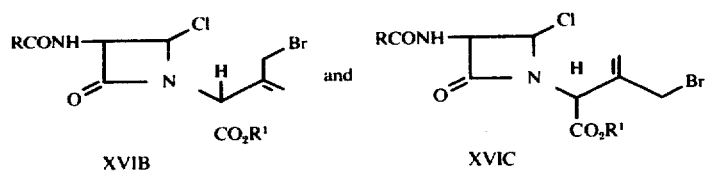

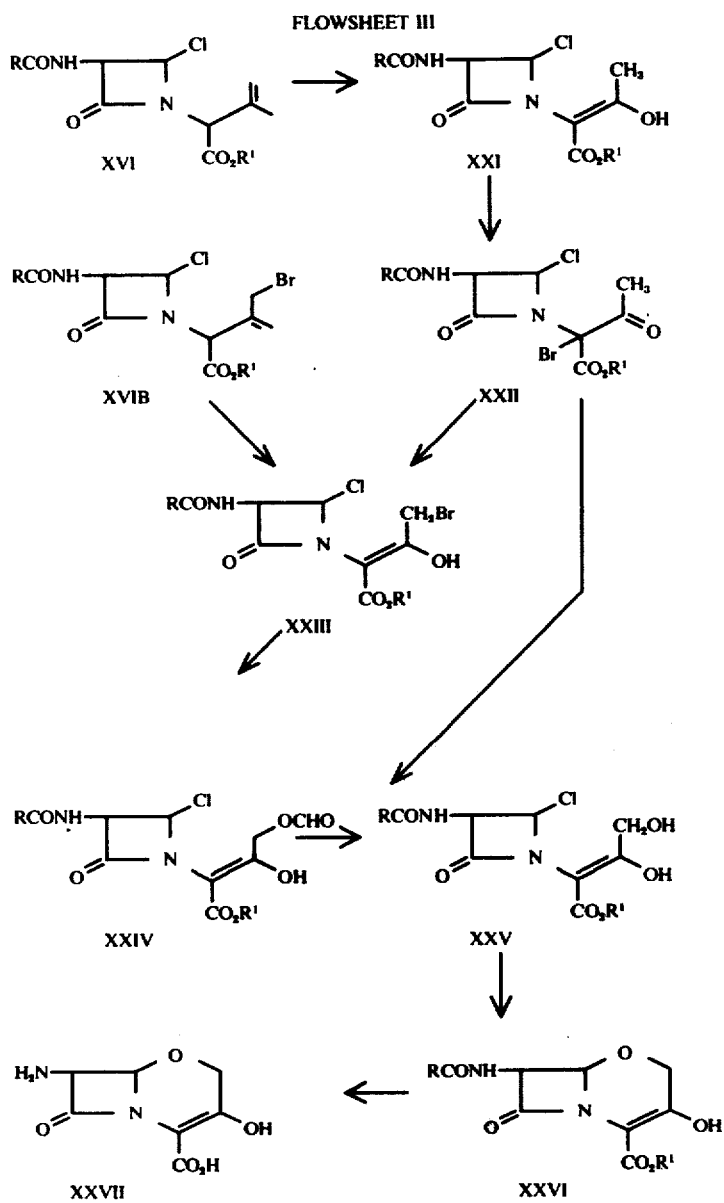

FLOWSHEET III

The important intermediate XXIII which is the R¹ yl-2-(2'-chloro-3'$\underline{S}$-R-carbonylamino-4'-oxo)azetidinyl-3-oxo-4-bromobutanoate is reacted with tetramethylguanidinium formate in the manner described previously for the conversion of the mixture of compounds V and VI to the mixture of compounds VII and VIII thereby to form the R¹ yl-2-(2'-chloro-3'$\underline{S}$-R-carbonylamino-4'-oxo)azetidinyl-3-oxo-4-formyloxybutanonate XXIV. However, in contrast to the aforementioned interconversion, the formation of compound XXIV gives a sngle geometric isomer. Compound XXIV is then deformylated with dilute hydrochloric acid in the manner already described in Flowsheet I for the transformation of compound VII to IX to give compound R¹ yl-2-(2'-chloro-3'$\underline{S}$-R-carbonylamino-4'-oxo)azetidinyl-3-oxo-4-hydroxybutanoate XXV. Cyclization to the 3-hydroxy-4-carboxy-7$\underline{S}$-R-carbonylamino-1-oxa,5-aza-6$\underline{R}$-bicyclo[4,2,0]oct-3-en-8-one XXVI proceeds either in the presence of a Lewis acid catalyst, as described for the cyclization of compound IX to compound XII or by dissolution in an amine base such as preferably pyridine as described for cyclization of compound IX to XII (see Flowsheet II).

Compound XXVI can be readily converted to the most useful intermediate free amino derivative XXVII which is the 3-hydroxy-4-carboxy-7$\underline{S}$-amino-1-oxa,5-aza-6$\underline{R}$-bicyclo[4,2,0]oct-3-en-8-one by removal of the RCO-radical and the R¹ substituent by processes whose specific nature will depend upon the values R and R¹ and which are known to those skilled in the art.

The key intermediate XXIII can be obtained in two ways. In the first, ozonalysis of a mixture of R¹ 2R- and 2S-2-(2'-chloro-3'$\underline{S}$-R-carbonylamino-4'-oxo)azetidinyl-3-bromomethyl-3-butenoates (XVIB and XVIC) is followed by reductive work-up of the ozonide obtained with zinc in acetic acid. Alternatively, the azetidinone XVI is ozonized in the same manner to the important enolic R¹ yl-2-(2'-chloro-3'$\underline{S}$-R-carbonylamino-4'-oxo)azetidnyl-3-oxo-butanoate XXI. Halogenation of the latter compound XXI, for example, by bromination, provides the tertiary bromide XXII as a mixture of epimers which rearrange to the $R^1$ yl-2-(2'-chloro-3'S-R-carbonylamino-4'-oxo)azetidinyl-3-oxo-4-bromobutanoate in the presence of hydrobromic acid in a mixture of benzene and acetic acid. The bromide XXII may also be converted to XXIV upon treatment with formate ions in formic acid.

The present invention will be more fully understood by referring to the following examples.

EXAMPLE I

Step A

Bromination of methyl 2-(2'R-chloro-3'S-phthalimido-4-oxo)-azetidinyl-3-methyl-2-butenoate IV

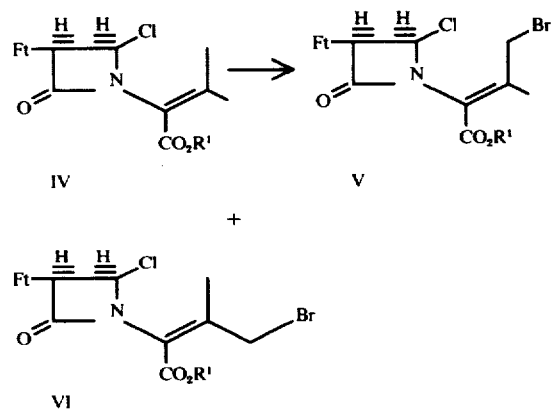

Ft= phthalimido

The methyl 2-(2'R-chloro-3'S-phthalimido-4'-oxo)-azetidinyl-3-methyl-2-butenoate (3.649 g, 10.1 m moles) was brominated with N-bromosuccinimide (1.958 g, 11.0 m moles, 1.1 molar equivalents) in $CCl_4$ (45 ml) containing benzoyl peroxide (10 mg). The reaction required 45 min. After cooling and removal of succinimide by filtration, the solution was passed through silica gel (30 g) and the column was eluted with 1.2 l of $CH_2Cl_2$. Evaporation of the eluate afforded 4.37 g of the mixed methyl 2-(2'R-chloro-3'S-phthalimido-4'-oxo)azetidinyl-trans-3-bromomethyl-2-butenoate (V) and methyl 2-(2'R-chloro-3'S-phthalimido-4'-oxo)azetidinyl-cis-3-bromomethyl-2-butenoate VI as a semi-crystalline mass.

Step B

Mixture of methyl 2-(2'R-chloro-3'S-phthalimido-4'-oxo)-azetidinyl-trans-3-formyloxymethyl-2-butenoate (VII) and methyl (2'R-chloro-3'S-phthalimido-4'-oxo)azetidinyl-cis-3-formyloxymethyl-2-butenoate (VIII)

The mixed bromides (4.37 g) of Step A were added to spectroscopic grade chloroform (40 ml) containing tetramethylguanidinium formate (8.0 g, 50 m moles) and this solution was stirred at room temperature for 15 hr. It was then washed twice with 50 ml portions of cold saturated NaCl, dried ($MgSO_4$) and evaporated. The residue, in benzene, was chromatographed on a column of 150 g of silica gel and this column was eluted successively with benzene (100 ml) petroleum ether (250 ml), petroleum ether:ethyl acetate (85:15, 250 ml), petroleum ether:ethyl acetate (80:20, 500 ml), petroleum ether:ethyl acetate (75:25, 250 ml) and petroleum ether:ethyl acetate (65:35). The eluant was collected in 50 ml fractions. Fractions 10–21, on combination and evaporation, gave unreacted azetidinone (IV) Z(600 mg, 16.5% recovery). Fractions 26–42 contained 2.193 g (64% based on recovered starting material) of a mixture of methyl 2-(2'R-chloro-3'S-phthalimido-4'-oxo)-azetidinyl-trans-3-fromyloxymethyl-2-butenoate (VII) and methyl 2-(2'R-chloro-3'S-phthalimido-4'-oxo)azetidinyl-cis-3-formyloxymethyl-2-butenoate (VIII) having a NMR spectrum similar to that published for that mixture in S. Wolfe et al Can. J. Chem. vol. 50, 1972 p. 2898.

Step C

Mixture of methyl 2-(2'R-chloro-3'S-phthalimido-4'-oxo)-azetidinyl-3-methyl-4-hydroxy-2-butenoate (IX) and 2-oxo-2,5-dihydro-3-(2'R-chloro-3'S-phthalimido-4'-oxo)azetidinyl-4-methylfuran (IXA)

The mixture obtained in Step B was dissolved in $CH_2Cl_2$ (10 ml), the solution cooled to 0° C, and 30 ml of ice-cold N methanolic HCl (prepared by dissolution of anhydrous HCl in absolute methanol) was added all at once. The mixture was stirred for 1.5 hr at 0°, then diluted with $CH_2Cl_2$, washed with cold saturated NaCl, water, and the organic layer dried ($MgSO_4$). The residue obtained upon evaporation of the solvent contained the lactone which is the 2-oxo-2,5-dihydro-3-(2'R-chloro-3'S-phthalimido-4'-oxo)azetidinyl-4-methylfuran (IXA) and the desired alcohol which is the methyl 2-(2'R-chloro-3'S-phthalimido-4'-oxo)azetidinyl-3-methyl-4-hydroxy-trans-2-butenoate (IX).

Step D

Mixture of methyl 2-(2'R-chloro-3'S-phthalimido-4'-oxo)azetidinyl-trans-3-(1-tetrahydropyranyloxymethyl)-2-butenoate (X) and 2-oxo-2,5-dihydro-3-(2'R-chloro-3'S-phthalimido-4'-oxo)azetidinyl-4-methylfuran (IXA)

Since the mixture obtained in Step C could not be separated by silica gel chromatography, the mixture was dissolved in benzene (30 ml, freshly distilled from sodium wire) containing 5 mg of anhydrous p-toluenesulfonic acid, and dihydropyran (1 ml, freshly distilled from KOH pellets) was added. This mixture was stirred at room temperature for 4 hr. Most of the solvent was then removed below 40° and $CH_2Cl_2$ (50 ml) was added. Extraction with ice-cold saturated NaCl containing some $NaHCO_3$, followed by drying ($MgSO_4$) and evaporation afforded a white foam containing a mixture of methyl 2-(2'R-chloro-3'S-phthalimido-4'-oxo)azetidinyl-trans-3-(1-tetrahydropyranyloxymethyl)-2-butenoate (X) and 2-oxo-2,5-dihydro-3-(2'R-chloro-3'S-phthalimido-4'-oxo)azetidinyl-4-methylfuran (IXA).

Step E

Isolation of methyl 2-(2'R-chloro-3'S-phthalimido-4'-oxo)-azetidinyl-trans-3-(1-tetrahydropyranyloxymethyl)-2-butenoate (X)

The foam obtained in Step D was chromatographed on a column of 85 g of silica gel prepared with 30°–60 ° petroleum ether. The column was eluted successively with petroleum ether (30°–60°):ethyl acetate 95:5 (200 ml), 90:10 (250 ml), 85:15 (500 ml), 80:20 (250 ml), 75:25 (250 ml), 70:30 (500 ml), 65:35. The compounds were eluted with this latter mixture, and 50 ml fractions were collected. Fractions 1–7 contained 970 mg of methyl 2-(2'R-chloro-3'S-phthalimido-4'- oxo)azetidinyl-trans-3-(1-tetrahydropyranyloxymethyl)-2-butenoate (X).

Step F

Methyl 2-(2'R-chloro-3'S-phthalimido-4'-oxo)azetidinyl-3-hydroxymethyl-trans-2-butenoate The tetrahydropyranyl ether of Step E (290 mg, 0.614 m mole) was dissolved in CH$_2$Cl$_2$(4 ml), and the solution was cooled to 0° C. Then ice-cold 1.2 N methanolic HCl (25 ml) was added, and the reaction mixture was stirred at 0° for 4 hr. It was diluted with CH$_2$Cl$_2$(25 ml) and washed several times with ice-cold NaCl, dried, and evaporated. The residue crystallized. Recrystallization from ether gave 213 mg (92%) of the methyl 2-(2'R-chloro-3'S-phthalimido-4'-oxo)azetidinyl-trans-3-hydroxymethyl-2-butenoate, m.p. 134.5°–135.5°. Anal. Calcd. for C$_{17}$H$_{15}$N$_2$O$_6$Cl: C, 53.90; H, 3.99; N, 7.40. Found: C, 54.09; H, 4.20; N, 7.44. The NMR spectrum has the following peaks: 7.79 (4H, d), 6.17 (1H, d, 4.0), 5.71 (1H, d, 4.0), 4.75 (1H, d, 12.5), 4.25 (1H, d, 12.5), 3.82 (3H, s), 2.78 (1H, s, exchanges with D$_2$O), 2.38 (3H, s).

Step G

3-Methyl-4-methoxycarbonyl-7S-phthalimido-1-oxa,5-aza-6S-bicyclo[4,2,0]oct-3-en-8-one

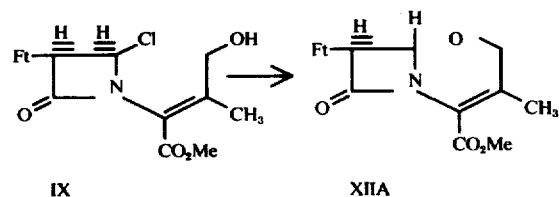

IX              XIIA

The methyl 2-(2'R-chloro-3'S-phthalimido-4'-oxo)azetidinyl-trans-3-hydroxymethyl-2-butenoate obtained in Step F (229 mg, 0.605 m mole) was dissolved in dimethoxyethane (15 ml, freshly distilled from lithium aluminium hydride), and anhydrous stannous chloride (150 mg, 0.834 m mole, 1.38 molar equivalents) was added. The mixture was stirred at room temperature for 24 hr, then diluted with CH$_2$Cl$_2$ and washed with brine. The aqueous extract was back-extracted twice with methylene chloride. The combined organic extracts were dried and evaporated to give 214 mg of a gum which crystallized on scratching. Recrystallization from hot chloroform-hexane or ether afforded 176 mg (86%) of the oxacephem XIIA having the trans configuration of the β-lactam protons. Anal. Calcd. for C$_{17}$H$_{14}$O$_6$N$_2$: C, 59.65; H, 4.12; N, 8.18. Found: C, 59.78; H, 3.94; N, 8.42.

The 1-oxacephem compound which is the 3-methyl-4-methoxycarbonyl-7S-phthalimido-1-oxa,5-aza-6S-bicyclo[4,2,0]-oct-3-en-8-one has the following properties: [a]$_D$$^{CHCl_3}$–16.9; m.p. 170°–171.5°; λ$_{max}$$^{EtOH}$ 226 (42000), 268 (14700)

NMR: 7.80 (4H, d), 5.33 (1H, d, 1.8 Hz), 5.27 (1H, d, 1.8 Hz), 4.37 (2H, s), 3.90 (3H, s), 2.03 (3H, s).
IR: λ$^{max}$(KBr): 5.61, 5.65, 5.79μ.

Cyclization to the same compound obtained in Step F was also achieved in tetrahydrofuran.

It was observed that HCl was evolved at the melting point of the alcohol. Therefore, 24 mg of the alcohol were heated at 150° under reduced pressure until gas evolution ceased. Cooling and crystallization of the black residue from ether afforded 15 mg of the 1-oxacephem described above.

Repetition of the stannous chloride cyclization in a more concentrated solution, and with a slight excess of anhydrous SnCl$_2$, afforded a 1:1 mixture of the above oxacephem and the isomer XIIB which is the 3-methyl-4-methoxycarbonyl-7S-phthalimido-1-oxa,5-aza-6R-bicyclo[4,2,0]oct-3-en-8-one of the formula:

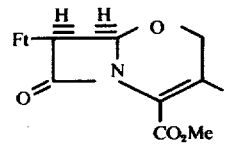

XIIB

Thus the alcohol (38 mg, 0.10 m mole) obtained in Step F and SnCl$_2$ (30 mg, 0.167 m mole), in anhydrous dimethoxyethane (5 ml) were stirred at room temperature for 20 hr. Isolation as above afforded material which was filtered rapidly through a short alumina column and then purified by preparative layer chromatography on silica gel (petroleum ether:ethyl acetate 65:35). The cis azetidinone XIIB has the following NMR spectrum: 7.80 (4H, d), 5.56 (1H, d, 3.8 Hz), 5.10 (1H, d, 3.8 Hz), 4.30 (2H), 3.90 (3H, s), 2.03 (3H, s).

Repetition of this experiment with 32 mg of alcohol of Step F and 25 mg of SnCl$_2$ in dry THF (5 ml) for 16 hr at room temperature afforded a 3:2 mixture of trans:cis oxacephems.

EXAMPLE II

Conversion of methyl 2-(2'S-chloro-3'S-phthalimido-4'-oxo) azetidinyl-3-methyl-2-butenoate into the Z-allylic alcohol

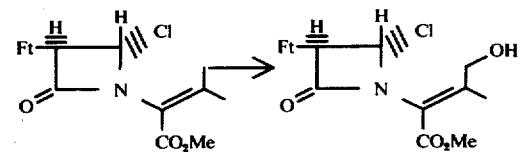

Step A

The methyl ester, prepared from 4.70 g (13.48 m moles) of the acid, was brominated with 2.640 g (14.82 m moles) of NBS in CCl$_4$ (50 ml). After 35 min of reflux the mixture was cooled, filtered, and the filtrate passed through a column of 45 g of silica gel. Elution with CH$_2$Cl$_2$ (1 l) and evaporation of the total eluate yielded a pale yellow foam, which was used directly for the next step.

Step B

In this step, the brominated material and tetramethylguanidinium formate (8.150 g, 50.5 m moles) were stirred at room temperature in reagent grade CH$_2$Cl$_2$ (100 ml) for 11 hr. Then additional CH$_2$Cl$_2$ (50 ml) was added, and the solution washed four times with saturated sodium chloride, dried, and evaporated. The resulting reddish-brown foam was chromatographed on 250 g of silica gel. The column was prepared with petroleum ether (30°–60°) and the material introduced in the minimum amount of $CH_2Cl_2$. Elution was performed with graded mixtures of petroleum ether:ethyl acetate, product appearing in the 35:65 eluate; at this point fractions of 100 ml were collected. Fractions 1-6 contained 685 mg of the original ester, methyl 2-(2'S-chloro-3'S-phthalimido-3'-oxo)azetidinyl-3-methyl-2-butenoate. Fractions 8-12 contained 2.681 g of the mixed Z- and E-formate esters which are the methyl 2-(2'S-chloro-3'S-phthalimido-4'-oxo)azetidinyl-trans- and cis-3-formyloxymethyl-2-butenoates having the structures:

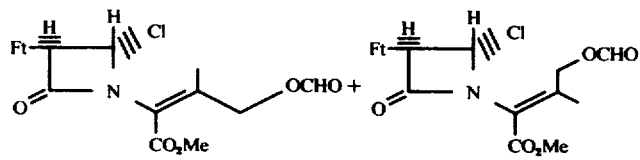

The NMR spectrum of this mixture has been published: S. Wolfe et al, op.cit. Based on recovered ester, the conversion of the starting material to these formate esters in two steps is 57%.

Step C

The mixture of formates was dissolved in spectroscopic grade $CH_2Cl_2$ (16 ml), the solution cooled to 0°, and 40 ml of 1.1 N anhydrous methanolic HCl, precooled to −10°, was added all at once. The resulting solution was stirred at 0° for 1.5 hr and then diluted with $CH_2Cl_2$ and washed once with ice-cold brine. The aqueous phase was extracted three times with $CH_2Cl_2$, and the combined organic extract dried and evaporated to a white foam.

Step D

This was dissolved in freshly dried benzene (30 ml) containing 5 mg of anhydrous p-toluenesulfonic acid, and dihydropyran (freshly distilled from KOH pellets, 1 ml) was then added. This mixture was stirred at room temperature. After 1 hr, 10 ml of $CH_2Cl_2$ were added, and stirring was continued for an additional 3.5 hr. The product was isolated by dilution with $CH_2Cl_2$, washing with ice-cold brine, containing some $NaHCO_3$, back extraction of the aqueous extract, and evaporation of the combined dried organic extract.

Step E

The yellow foam was chromatographed on 150 g of silica gel in the same manner as described above. Material was eluted with a 65:35 petroleum ether:ethyl acetate mixture. The first fractions contained 931 mg (30.4% from the mixed formate esters) of the tetrahydropyranyl THP ether of the structure:

The final fractions contained 1.406 g (61.2% from the mixed formate esters) m.p. 147.5°–148.5° after recrystallization from $CH_2Cl_2$-ether, of the lactone which is the 2-oxo-2,5-dihydro-3-(2'S-chloro-3'S-phthalimido-4'-oxo)azetidinyl-4-methylfuran.

The NMR spectrum of the lactone has been discussed by S. Wolfe et al, op. cit.

The NMR spectrum of the THP ether has peaks at 7.84 (4H, d), 6.29 (1H, d, 1.5 Hz), 5.60 (1H, d, 1.5 Hz), 4.66 (1H, br s), 4.41 (2H, s), 3.86 (3H, s), 3.83 (2H, s), 2.37 (3H, s), 1.67 (6H, br s).

Step F

The tetrahydropyranyl ether was dissolved in spectroscopic grade $CH_2Cl_2$ (10 ml), the solution cooled to 0°, and 40 ml of precooled (−10°) 0.96 M anhydrous methanolic HCl was added all at once. The mixture was stirred at 0° for 1.5 hr and then extracted with ice-cold brine. The aqueous phase was back-extracted twice with $CH_2Cl_2$ and the combined $CH_2Cl_2$ extracts were dried and evaporated. The alcohol, which is the methyl 2-(2'S-chloro-3'S-phthalimido-4'-oxo)azetidinyl-trans-3-hydroxymethyl-2-butenoate (809 mg, 106%) did not crystallize. Its NMR spectrum has the following peaks: 7.75 (4H, d), 6.18 (1H, d, 1.5 Hz), 5.55 (1H, d, 1.5 Hz), 4.30 (1H, d, 13 Hz), 4.27 (1H, d, 13 Hz), 3.85 (3H, s), 3.17 (1H, br s), 2.35 (3H).

Step G

Interconversion of the 2'S and 2'R-chloro Z-tetrahydropyranyl ethers

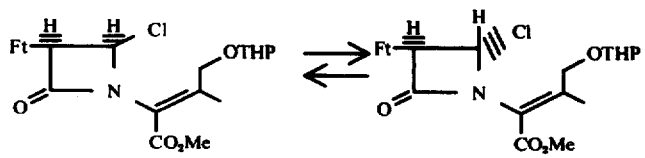

The crystalline tetrahydropyranyl ether of the 2'R series (cis) (92 mg, 0.199 m mole) and tetraethylammonium chloride (165 mg, 1 m mole) were refluxed for 18 hr in dry acetone (14 ml). The mixture was then diluted with saturated NaCl and extracted with $CH_2Cl_2$. The organic extract was dried and evaporated. The NMR spectrum of the residue showed it to be a 1:1 mixture of 2'R and 2'S epimers.

This experiment demonstrates that epimerization and displacement of a substituent at the 2' position is possible following oxidation of the Z-methyl group.

Step H

Cyclization of methyl 2-(2'S-chloro-3'S-phthalimido-4'-oxo) azetidinyl-trans-3-hydroxymethyl-2-butenoate to a 1-oxacephem

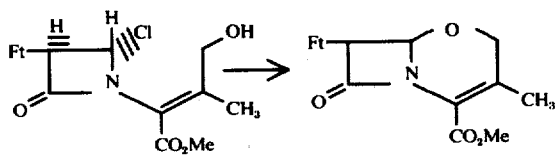

The alcohol (95 mg, 0.25 m mole) and anhydrous stannous chloride (75 mg, 0.42 m mole) were stirred at room temperature in freshly dried dimethoxyethane (5 ml) for 20 hr. Isolation afforded 75 mg (88%) of the same trans-1-oxacephem described in Example I.

EXAMPLE III

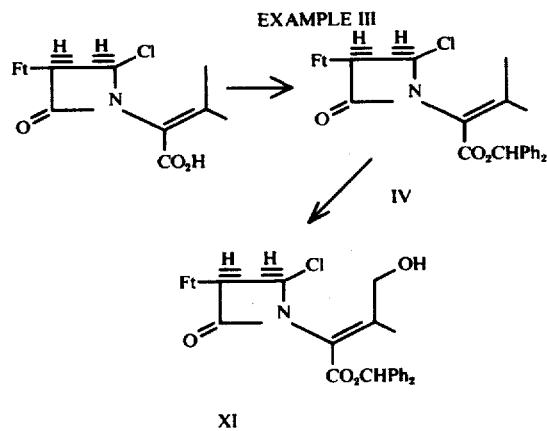

Step A

The 2-(2'R-chloro-3'S-phthalimido-4'-oxo)azetidinyl-3-methyl-2-butenoic acid (6.056 g, 17.35 m moles) and diphenyldiazomethane (3.93 g. 20.2 m moles) were dissolved in chloroform (70 ml). When the initial gas evolution had ceased, the solution was refluxed for 4 hr and then evaporated to dryness. The benzhydryl ester was recrystallized from $CH_2Cl_2$-ether, m.p. 186°-187.5°. The NMR spectrum has the following peaks: 7.87 (4H, d), 7.37 (10H), 6.98 (1H, s), 6.03 (1H, d, 4 Hz), 5.60 (1H, d, 4 Hz), 2.37 (3H, s), 2.33 (3H, s).

In an exploratory experiment, the benzhydryl ester (241 mg, 0.469 m mole) was brominated in $CCl_4$ (8 ml) with N-bromosuccinimide (92 mg, 0.516 m mole). The reaction was terminated after 20 min. and, after removal of succinimide by filtration, the solvent was evaporated. The product was purified by p.l.c. to give 171 mg of material, whose NMR spectrum showed it to be a 1.7:1 mixture of monobrominated compounds having the structures:

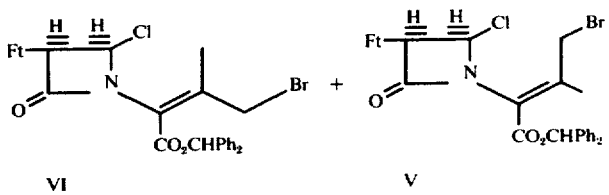

This NMR spectrum had peaks at 7.83 (4H), 7.35 (10H), 7.03 (0.63 H, s), 7.00 (0.37 H, s), 6.07 and 6.03 (2 doublets, 4.0 Hz, 1H), 5.63 (1H, d, 4.0 Hz), 4.78-4.25 (2H, m), 2.45 (1.9 H, s), 2.02 (1.1 H, s).

Step B

The mixture of monobromides obtained in Step A was dissolved in $CH_2Cl_2$ (5 ml) containing tetramethylguanidinium formate (76 mg, 0.47 m mole). The solution was left for 24 hr and then diluted with $CH_2Cl_2$ and washed with brine. The aqueous phase was back-extracted with $CH_2Cl_2$ and the combined organic layers, after drying, were evaporated. The residue was subjected to p.l.c. on silica gel; elution with 3:1 petroleum ether:ethyl acetate afforded two fractions. The more mobile (47 mg, 27.5% of the original mixture of bromides) was unreacted monobromide, but the ratio of peaks at 2.45 and 2.02 was 2.8:1, indicating that one of the bromides reacts more rapidly with formate ions. The less mobile fraction (62 mg, 52%) was a 3:1 mixture of formate esters, which are the benzhydryl 2-(2'R-chloro-3'S-phthalimido-4'-oxo)azetidinyl-trans- and cis-3-formyloxymethyl-2-butenoates:

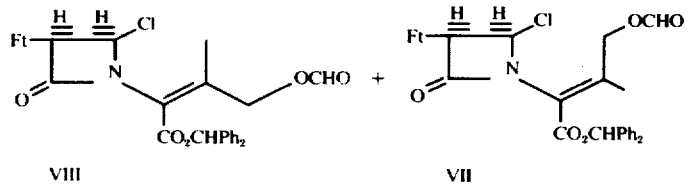

VIII          VII

The NMR spectrum of this mixture has the following peaks: 8.22 (0.25 H, s), 8.10 (0.75 H, s), 7.83 (4H, d), 7.37 (10H), 7.03 (1H, s), 6.13 (1H, d, 4.0 Hz), 5.68 (1H, d, 4.0 Hz), 5.37 (2H, br s), 2.37 (2.2 H, s), 2.32 (0.8 H, s).

The bromination and conversion to formate esters was now repeated on a larger scale, without purification after the bromination step. The benzhydryl ester (6.240 g, 12.1 m moles) was reacted in CCl₄ (160 ml) for 10 min with N-bromosuccinimide (2.365 g, 13.3 m moles). The material obtained, following cooling, filtration and evaporation of the solvent, was dissolved in spectroscopic grade CH₂Cl₂ (150 ml) containing tetramethylguanidinium formate (8.0 g, 49.6 m moles). This solution was stirred for 4.5 hr and then washed with cold brine. The aqueous phase was back-extracted twice with CH₂Cl₂ and the combined organic extract, after drying was evaporated. The residue was chromatographed on a column of 250 g of silica gel. Elution was performed with graded mixtures of petroleum ether and ethyl acetate. Material appeared with a 70:30 ratio of these solvents, and this mixture was then maintained, 100 ml fractions being collected. Fractions 1-10 contained 2.097 g of a mixture of starting material and monobromides. Fractions 14-24 contained a total of 2.673 g of a 2:1 mixture of the formates (39.2% from the benzhydryl ester).

Step C

The mixture of formate esters (2.610 g), in CH₂Cl₂ (15 ml), was cooled to 0° C and then 40 ml of precooled (−10°) N anhydrous methanolic HCl was added in one portion. The resulting solution was stirred at 0° for 1.2 hr. It was then poured onto a mixture of brine and ice and extraction performed three times with 50 ml portions of CH₂Cl₂. The CH₂Cl₂ extract was then dried and evaporated. Examination of the residue by t.l.c. and NMR showed benzhydrol, alcohol and lactone. The residue was dissolved in dry CH₂Cl₂ (50 ml) containing dihydropyran (1 ml, freshly distilled) and anhydrous p-toluenesulfonic acid (2 mg). This solution was stirred for 4 hr at room temperature and then washed with ice-cold brine containing sufficient bicarbonate to ensure a slightly alkaline medium. The aqueous phase was twice back-extracted with CH₂Cl₂ and the combined CH₂Cl₂ layers dried and evaporated to a white foam. This was chromatographed on 110 g of silica gel. Elution with graded mixtures of petroleum ether-ethyl acetate afforded the tetrahydropyranyl ether of benzhydrol in the 85:15 mixture, and the remainder of the materials in the 65:35 mixture. Fractions of 50 ml were collected. Fractions 1-6 contained 828 mg (28.9% from the formate esters) of the tetrahydropyranyl ether X which is the benzhydryl 2-(2'R-chloro-3'S-phthalimido-4'-oxo)azetidinyl-trans-3-(1-tetrahydropyranyloxymethyl)-2-butenoate:

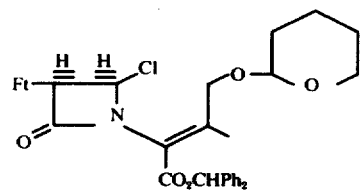

X

Fractions 19-24 contained 1.012 g (63%) of the previously-described lactone:

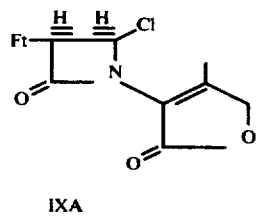

IXA

The NMR spectrum of the THP ether has the following peaks: 7.74 (4H, d), 7.27 (10H), 6.88 (1H, s), 5.93 (1H, d, 4.0 Hz), 5.52 (1H, d, 4.0 Hz), 4.80 (2H, br s), 4.58 (1H, s), 3.83 (2H, br s), 2.38 (3H, s), 1.63 (6H, m).

Step D

The tetrahydropyranyl ether protecting group was removed, as described above, in methanolic HCl to give 693 mg of the alcohol as a white foam. The structure of this compound is:

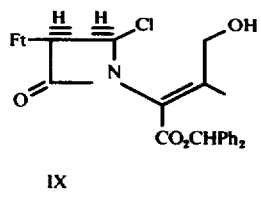

IX

Its NMR spectrum has peaks at 7.83 (4H, d), 7.25 (10H), 7.00 (1H, s), 6.08 (1H, d, 4 Hz), 5.80 (1H, d, 4 Hz), 4.52 (1H, d, 14 Hz), 4.08 (1H, d, 14 Hz), 2.80 (1H, br s), 2.38 (3H, s).

Step E

Cyclization of benzhydryl 2-(2'R-chloro-3'S-phthalimido-4'oxo)azetidinyl-trans-3-hydroxymethyl-2-butenoate to a 1-oxacephem

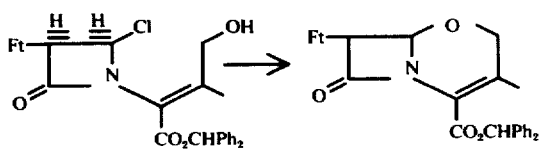

The alcohol (100 mg, 0.188 m mole) and anhydrous stannous chloride (34 mg, 0.188 m mole) were stirred at room temperature in dry dimethoxyethane for 13 hr. The isolated product was purified by p.l.c. (3:1 petroleum ether:ethyl acetate) to give the oxacephem, which is the 3-methyl-4-benzhydryloxycarbonyl-7S-phthalimido-1-oxa, 5-aza-bicyclo [4,2,0]oct-3-en-8-one.

The NMR spectrum has peaks at 7.68 (4H, d), 7.23 (10H), 6.83 (1H), 5.20 (1H, d, 1.5 Hz), 5.13 (1H, d, 1.5 Hz), 4.26 (2H), 1.97 (3H).

EXAMPLE IV

Functionalization of the methyl groups of benzhydryl 2-(2'R-chloro-3'S-trichloroethoxycarbonylamino-4'-oxo)azetidinyl-3-methyl-2-butenoate

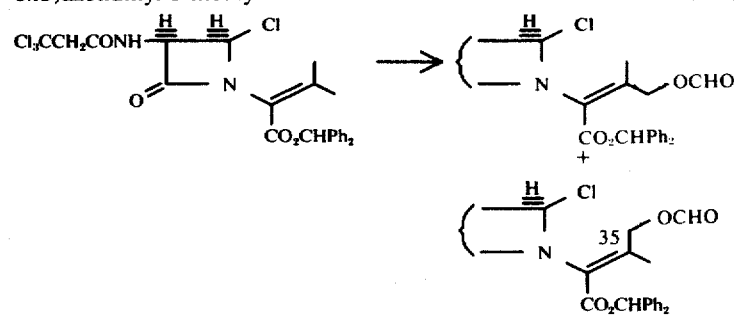

The benzhydryl ester (691 mg, 1.235 m moles) was brominated in CCl₄ (20 ml) for 30 min with NBS (250 mg, 1.40 m moles). The brominated product was isolated by p.l.c. (petroleum ether:ethyl acetate 4:1) and dissolved in methylene chloride (10 ml) containing tetramethylguanidinium formate (1 g, a large excess). After 2 hr this solution was washed with brine, dried and evaporated. Purification by p.l.c. on silica gel (petroleum ether-ethyl acetate 85:15) afforded 125 mg of the allylic formates which are the benzhydryl 2-(2'R-chloro-3'S-trichloroethoxycarbonylamino-4'-oxo)azetidinyl-trans- and cis-3-formyloxymethyl-2-butenoates. The NMR spectrum has peaks at: 8.05 (1H, br), 7.33 (10H), 6.92 (1H), 5.93 (1H, d, 4.0 Hz), 5.40 (1H, d, 4.0 Hz), 5.30 (2H), 5.23 (2H), 2.05 (3H).

This experiment establishes a sequence in which removable blocking groups are present on both nitrogen and carboxyl.

EXAMPLE V

Removal of the trichloroethoxycarbonyl protecting group

Benzhydryl 2-(2'R-chloro-3'S-trichloroethoxycarbonylamino-4'-oxo)azetidinyl-3-methyl-2-butenoate (1.250 g, 2.23 mmoles) was dissolved in acetonitrile (25 ml), the solution cooled to 0° C, and ice-cold 88% formic acid (75 ml) was added, followed by 4 g of zinc dust. The mixture was stirred mechanically for 3 h, by which time the starting material had reacted completely. The insoluble material was removed by filtration and washed with ethyl acetate. The combined filtrates were concentrated below 25° and the last traces of water and formic acid removed by azeotropic drying with benzene. The resulting yellowish-orange oil was dissolved in methylene chloride, shaken successively with an ice-cold solution of sodium bicarbonate and sodium chloride, water, and dried. The pale green solution was treated with decolorizing carbon for 30 min at room temperature and then filtered through Celite. Evaporation afforded 819 mg of benzhydryl 2-(2'R-chloro-3'S-amino-4'-oxo)azetidinyl-3-methyl-2-butenoate (819 mg, 95%) as a pale yellow foam. NMR: 7.29 (10H, s), 6.90 (1H, s), 5.87 (1H, d, 4.0), 4.48 (1H, d, 4.0), 2.30 (3H, s), 2.00 (3H, s), 1.95 (2H, br).

The equation for the above-mentioned reaction is:

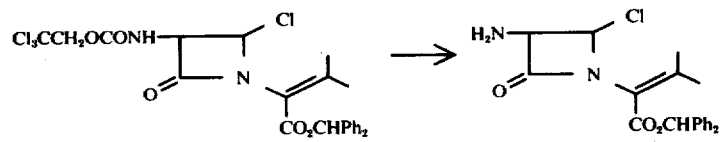

EXAMPLE VI

Benzhydryl 2-(2'R-chloro-3'S-trichloroethoxycarbonylamino-4'-oxo)azetidinyl-trans-3-hydroxymethyl-2-butenoate The mixture of allylic formates prepared in Example IV (125 mg) was dissolved in CH₂Cl₂ (10 ml), the solution cooled to 0° C, and 3 ml of ice-cold N methanolic HCl was added. After 1.5 hr at 0°, the mixture was washed with cold brine and water, dried over anhydrous magnesium sulfate, and evaporated. The residue was dissolved in dry benzene (5 ml) containing 1 mg of anhydrous p-toluenesulfonic acid, and freshly distilled dihydropyran (0.2 ml) was added. After 2 hr at room temperature, most of the solvent was removed under reduced pressure and CH₂Cl₂ (10 ml) was added. The solution was extracted with a mixture of cold brine and NaHCO₃, dried and evaporated to a white foam. Chromatography on silica gel afforded 52 mg of benzhydryl 2-(2'R-chloro-3'S-trichloroethoxycarbonylamino-4'-oxo-)azetidinyl-trans-3-(1-tetrahydropyranyloxymethyl)-2-butenoate.

This compound was converted to a 70:30 mixture of 2'S and 2'R chloro epimers upon heating in CHCl₃ (10 ml) with tetramethylguanidinium chloride (500 mg) for 3 hr.

The mixture of epimers was dissolved in CH₂Cl₂ (2 ml), the solution cooled to 0°, and ice-cold N methanolic HCl (5 ml) was added. After stirring at 0° for 4 hr, the mixture ws diluted with CH₂Cl₂ (25 ml), washed with ice-cold brine, and evaporated to give benzhydryl 2-(2'-chloro-3'S-trichloroethoxycarbonylamino-4'-oxo)azetidinyl-trans-3-hydroxymethyl-2-butenoate as a 70:30 2'S:2'R mixture of epimers.

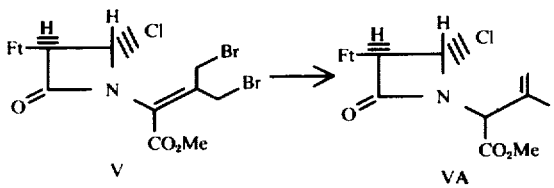

EXAMPLE VII

3-Methyl-4-benzhydryloxycarbonyl-7S-trichloroethoxycarbonylamino-1-oxa,5-aza-6R-bicyclo[4,2,0]oct-3-ene-8-one A 70:30 2'S:2'R mixture of benzhydryl 2-(2'-chloro-3'S-trichloroethoxycarbonylamino-4'-oxo)azetidinyl-trans-3-hydroxymethyl-2-butenoates (500 mg) was dissolved in pyridine (5 ml). After 6 hr at room temperature, the solution was diluted with water (50 ml) and methylene chloride (25 ml), and the methylene chloride layer was withdrawn. This was washed exhaustively with N HCl, dried and evaporated. Chromatrography on silica gel afforded 140 mg of the oxacephem having the 6Rconfiguration.

EXAMPLE VIII

3-Methyl-4-carboxy-7S-amino-1-oxa,5-aza-6R-bicyclo[4,2,0]oct-3-en-8-one (oxa-7-ADCA).

The oxacephem described in Example VII (140 mg) was dissolved in acetonitrile (5 ml), the solution cooled to 0° C, and ice-cold 88% formic acid (7 ml) was added, followed by 0.5 g of zinc dust. After 3 hr of stirring at 0°, insoluble material was removed by filtration, washed with ethyl acetate, and the combined filtrates were concentrated below 25°, the last traces of water and formic acid being removed by azeotropic drying with benzene. The residue was dissolved in CH₂Cl₂ (10 ml) and washed successively with NaHCO₃, brine and water, and dried to give 3-methyl-4-benzhydryloxycarbonyl-7S-amino-1-oxa,5-aza-6R-bicyclo[4,2,0]oct-3-en-8-one. This compound (90 mg) was dissolved in trifluoroacetic acid (2 ml). After 5 min at room temperature, the solution was evaporated to dryness. The residue was triturated with ether, and the ethersoluble material was discarded. Water (0.5 ml) was then added, followed by solid sodium bicarbonate, in portions, until the 1oxa-7-amino-descacetoxycephalosporanic acid (oxa-7-ADCA) precipitated (XX).

EXAMPLE IX

Step A

Debromination of methyl 2-(2'S-chloro-3'S-phthalimido-4'-oxo)azetidinyl-3-bromomethyl-4-bromo-2-butenoate The dibromide (203 mg, 0.39 m mole) was mixed with powdered zinc dust (112 mg, 1.71 g atoms, 4.4 equivalents) in a flask suspended in an ice-bath. Then glacial acetic acid (20 ml) was cooled until it began to freeze, and this was added to the mixture of the dibromide and zinc. The reaction mixture was swirled vigorously in the ice-bath for 4 min. and was then poured into an ice-cold mixture of CH₂Cl₂ (50 ml) and water (10 ml). The organic layer was washed thoroughly with water, dried (MgSO₄) and evaporated to give the methyl 2-(2'S-chloro-3'S-phthalimido-4'-oxo)azetidinyl-3-methyl-3-butenoate as a colorless foam (128 mg, 90%). In subsequent experiments a 4:1 acetonitrile:acetic acid mixture was employed as the solvent.

The NMR spectrum shows peaks at 7.77 (4H), 5.95 (0.5 H, d, 2 Hz), 5.88 (0.5 H, d, 2 Hz), 5.57 (0.5 H, d, 2 Hz), 5.47 (0.5 H, d, 2 Hz), 5.25 (1H, br s), 5.15 (1H, br s), 4.83 (0.5 H, s), 4.22 (0.5 H, s), 3.83 (1.5 H, s), 3.80 (1.5 H, s), 2.00 (3H, br s). The spectrum is that of a 1:1 mixture of A and B. Since the isopropenyl moieties of the thiazoline (C) and the thiol ester (D) shown below do not have peaks above δ = 4.8, the singlets at 4.83 and 4.22 in the NMR spectrum of the β,γ-unsaturated compound may tentatively be assigned to A and B, respectively.

Step B

Epoxidation of the β,γ-unsaturated isomer of the trans-series

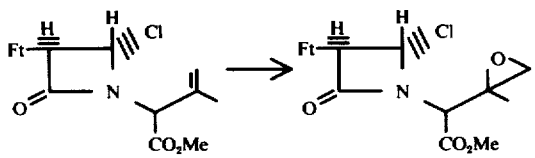

The olefin (235 mg, 0.65 m mole) and disodium hydrogen phosphate (0.5 g, 3.5 m moles) were stirred at room temperature in $CH_2Cl_2$ (15 ml) and 5 ml of a 0.4 M solution of peroxytrifluoroacetic acid in $CH_2Cl_2$ was added dropwide during 5 min. The mixture was stirred for 1 hr, filtered and washed with water. Evaporation of the dried $CH_2Cl_2$ layer gave 250 mg of a colorless foam which is the methyl 2-(2'S-chloro-3'S-phthalimido-4'-oxo)azetidinyl-3-methyl-3-butenoate oxide. In a second experiment, 334 mg (0.92 m mole) of the olefin was oxidized for 1.5 hr with 10 ml of 0.35 M $CF_3CO_3H$ in the presence of 0.9 g (6.3 m moles) of $Na_2HPO_4$. The resulting colorless foam weighed 312 mg. Both products had the same NMR spectrum: 7.60 (4H), 6.05 and 5.95 (2 doublets, 1H, 2.0), 5.43 (1H, d, 2.0), 4.8-4.2 (4 singlets, 1H), 3.78 (3H, br s), 3.03-2.72 (2H, m), 1.58 (3H, s).

Step C

Rearrangement of the epoxide of the trans-series with triethylamine

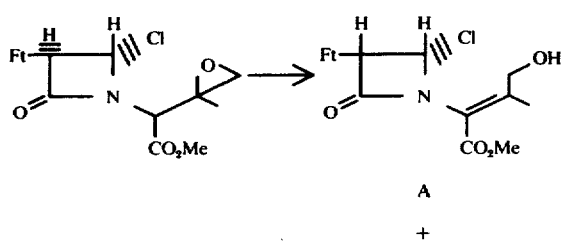

A

+

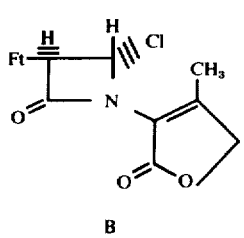

B

The epoxide (52 mg), in $CH_2Cl_2$ (3 ml), was treated with 5 drops of triethylamine. Evaporation after 5 min afforded a pale yellow foam whose NMR spectrum showed it to consist mainly of the lactone B (S. Wolfe, W. S. Lee, J. B. Ducep, and G. Kannengiesser, Can. J. Chem., 50, 2898 (1972)).

Repetition of the experiment in absolute methanol led, in addition to B, to the allylic alcohol A (b NMR).

EXAMPLE X

Effect of time upon the reaction of methyl 2-(2'S-chloro-3'S-phthalimido-4'-oxo)azetidinyl-3-bromo-methyl-4-bromo-methyl-2 butenoate with zinc in acetic acid

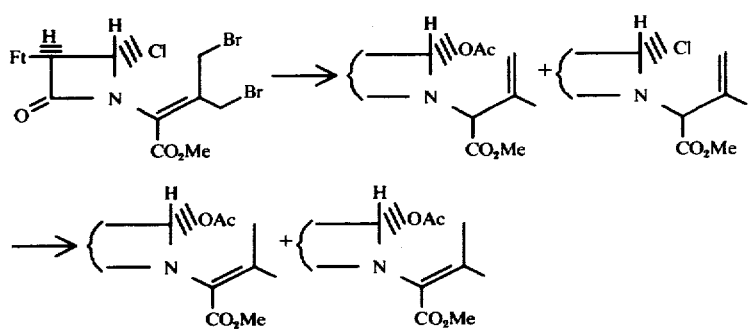

The dibromide (549 mg, 1.05 m moles) and zinc dust (158 mg, 2.42 g atoms) were mixed in a flask maintained in an ice-bath. Then glacial acetic acid (10 ml) was added, and the mixture was stirred until the zinc dissolved (30 min). Isolation as described above afforded 341 mg of a colorless foam whose NMR spectrum showed a peak at 2.12 in addition to the peaks of the $\beta,\gamma$-unsaturated isomer. The ratio of the peaks at 2.00 and 2.12 was 1.6:1. Repetition of the experiment with 205 mg (0.39 m moles) of the dibromide, 102 mg (1.65 g atoms) of zinc dust, and a 20 min reaction time, afforded 129 mg of a colorless foam. In this experiment the ratio of peaks at 2.00 and 2.12 was 3.5:1. The mixture having a 1.6:1 ratio of peaks at 2.00 and 2.12 (71 mg), in $CH_2Cl_2$ (5 ml), was treated with 5 drops of triethylamine. Evaporation of the solvent after 1 min afforded a yellow foam which was filtered through silica gel using 1:1 $CH_2Cl_2$:ether. The product was a mixture of 2'S-chloro and 2'S-acetoxy compounds. The NMR spectrum of the latter material has been described by S. Wolfe and M. P. Goeldner, Tetrahedron Letters, 5131 (1973).

Thus, when the dibromo compound is employed as the substrate, the 2'chloro substituent undergoes some displacement by acetoxy at longer reaction times.

EXAMPLE XI

Conversion of a monobrominated $\alpha,\beta$-unsaturated compound into a debrominated $\beta,\gamma$-unsaturated compound

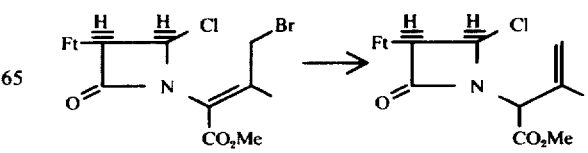

-continued
+

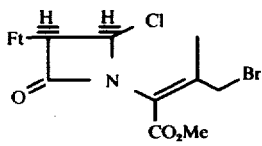

The α,β-unsaturated isomer was brominated with 1 molar-equivalent of NBS to give a product containing some unreacted material, some dibrominated material and, mainly (> 80%), the 1:1 mixture of monobrominated compounds. Treatment with zinc dust in glacial acetic acid in the usual way produced the β,γ-unsaturated isomer containing 10-15% of the α,β-unsaturated isomer.

This experiment demonstrates that an allylic monobromide can be converted into the β,γ-unsaturated isomer. However, since the monobromination cannot be controlled to avoid formation of the dibromide (and, therefore, the presence of α,β-isomer) the final product will be contaminated by this unreacted α,β-isomer. Consequently, it is more efficient to prepare the β,γ-isomer from the dibromide to ensure complete removal of the α,β-isomer.

EXAMPLE XII

Debromination of methyl 2-(2'R-chloro-3'S-phthalimido-4'-oxo)-3-bromomethyl-4-bromo-2-butenoate with a limited amount of zinc dust

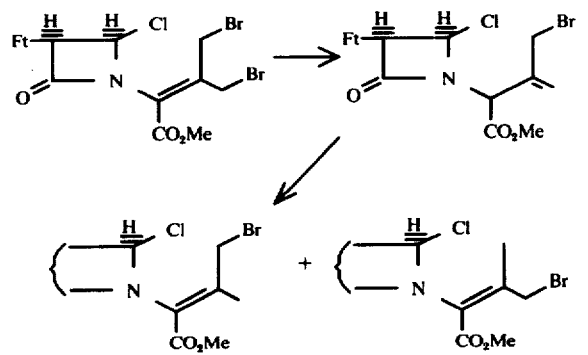

The dibromo compound (213 mg, 0.41 m mole) and zinc dust (26.8 mg, 0.41 g atom) were reacted in glacial acetic acid (5 ml) at 10° C. for 5 min. Isolation gave a colorless foam (125 mg). The NMR spectrum of this mixture showed the $CO_2CH_3$ and allylic $CH_3$ absorptions of the β,γ-unsaturated compound, but the ratio was 4:1 instead of the usual 1:1, indicating that the product contained only 20% of this compound. Treatment of the mixture with triethylamine in the usual manner led to a new material whose NMR spectrum revealed it to be a 2:1:1 mixture of

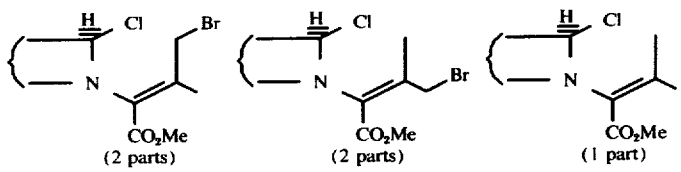

This experiment demonstrates that the debromination of the dibromide can be effected in two stages and that the β,γ-unsaturated monobromide which is the methyl 2-(2'R-chloro-3'S-phthalimido-4'-oxo)azetidinyl-4-bromo-3-butenoate can be isomerized to the α,β-unsaturated monobromide.

EXAMPLE XIII

Step A

Debromination of methyl 2-(2'R-chloro-3'S-phthalimido-4'-oxo)azetidinyl-3-bromomethyl-4-bromo-2-butenoate

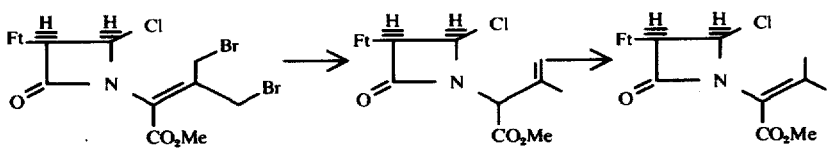

The dibromo compound (114 mg, 0.22 m mole) and zinc dust (63 mg, 0.97 g atom) were mixed in a round bottomed flask maintained in an ice-bath. Then 10 ml of precooled glacial acetic acid was added and the mixture was swirled vigorously for 4 min. Isolation of the product in the usual manner afforded 60 mg (78%) of the β,γ-isomer as a mixture of epimers. Treatment of this mixture with triethylamine, as described above, produced the α,β-unsaturated isomer, which is the methyl 2-(2'R-chloro-3'S-phthalimido-4'-oxo)azetidinyl-3-methyl-3-butenoate in 96% yield.

The NMR spectrum of the mixture of β,γ-unsaturated isomers has peaks at 7.92 (4H, d), 6.43 (0.5 H, d, 4.0), 6.05 (0.5 H, d, 4.0), 5.76 (0.5 H, d, 4.0), 5.74 (0.5 H, d, 4.0), 5.27 (2H, br s), 5.14 (0.5 H, s), 4.76 (0.5 H, s), 3.85 (3H, s), 2.05 (3H, br s).

Step B

Epoxidation of the β,γ-unsaturated isomer of the cis-series

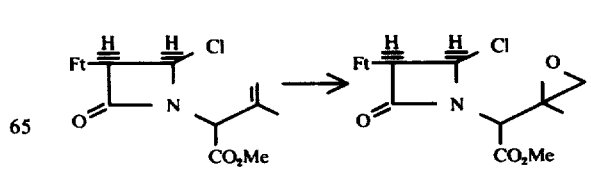

VA            VI

The olefin (240 mg, 0.65 m mole) and disodium hydrogen phosphate (0.5 g, 3.5 m moles) were stirred at room temperature in $CH_2Cl_2$ (20 ml), and 5 ml of a 0.4 M solution of peroxytrifluoroacetic acid in $CH_2Cl_2$ was added. The mixture was stirred for 1.5 hr (it remained acidic throughout this period) and then diluted with $CH_2Cl_2$ (80 ml). After thorough washing with water and drying ($MgSO_4$), the solvent was removed to give 210 mg of a colorless foam which is the methyl 2-(2'R-chloro-3'S-phthalimido-4'-oxo)azetidinyl-3-methyl-3-butenoate oxide.

The epoxide has the following NMR spectrum: 4.64 (4H, d), 6.33 and 5.85 (2 doublets, 1H, 4.0), 5.60 (1H, d, 4.0), 4.78, 4.68, 4.53, 4.13 (4 singlets, 1H), 3.78 (3H, br s), 2.87 (2H, m), 1.62 (3H, br s). The compound can be identified as the epoxide from the shift of the allylic methyl group and the presence of the series of peaks at 2.87.

Step C

Rearrangement of the epoxide of the cis-series with triethylamine

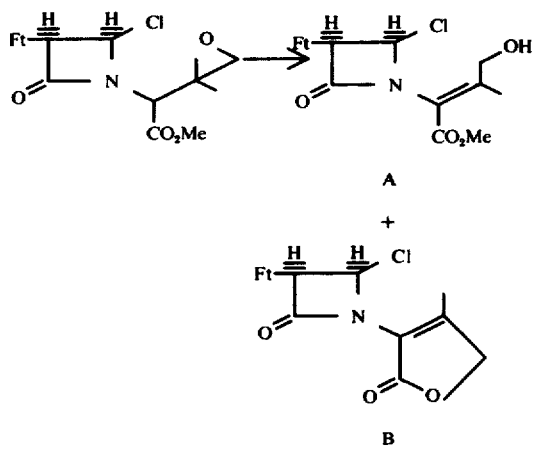

The epoxide (100 mg, 0.26 m mole) was added to absolute methanol (10 ml) containing triethylamine (40 mg, 0.4 m mole). The resulting bright yellow solution was stirred at 0° C. until the epoxide had reacted completely (1.2 hr). Evaporation of the solvent gave a residue whose NMR spectrum showed it to be a 3:1 mixture of the lactone B (S. Wolfe et al, op. cit.) and the Z-allylic alcohol A. The mixture was dissolved in benzene (15 ml, freshly distilled form sodium wire) containing freshly distilled dihydropyran (1 ml) and anhydrous p-toluenesulfonic acid (4 mg). This was stirred at room temperature for 4 hr. The solvent was then removed and the residue, in $CH_2Cl_2$ (25 ml), was washed with an ice-cold solution containing $NaHCO_3$ and NaCl and then dried. Removal of the solvent afforded (by t.l.c.) a mixture of the lactone B and the tetrahydropyranyl ether of A, which was separated by p.l.c. on silica gel (elution with 30:70 ethyl acetate:petroleum ether) into the lactone (40 mg, colorless needles, m.p. 126°–128°, after recrystallization from ether-petroleum ether) and the THP-ether (17 mg, m.p. 115°–116° after recrystallization from ether-petroleum ether). The structure of this compound is:

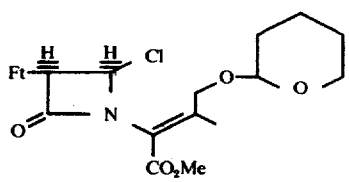

EXAMPLE XIV

Step A

Preparation of anhydro-2,2',2''-trichloroethoxycarbonyl penicillin

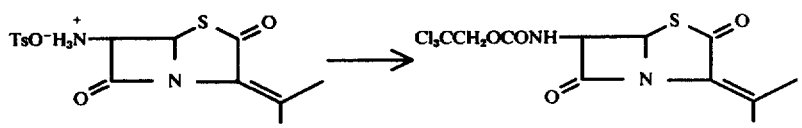

A cold (ice-salt bath) stirred suspension of the p-toluenesulfonic acid salt of anhydro-6-aminopenicillin (3.50 g, 9.45 mmoles) in methylene chloride (75 ml) was treated simultaneously with a solution of pyridine (0.835 g, 10.6 mmoles) in methylene chloride (20 ml) and 2,2,2-trichloroethoxychloroformate (2.16 g, 10.3 mmoles) in methylene chloride (20 ml). After the addition was complete (0.25 h), the homogeneous reaction mixture was stirred for an additional 0.5 h and then washed with cold 0.1 N hydrochloric acid (50 ml) and ice-water (50 ml). The organic layer was dried and evaporated under reduced pressure to give a white foam (3.41 g). NMR: 6.30 (1H, d, 8.5), 5.70 (1H, q, 8.5, 4.0), 5.62 (1H, d, 4.0), 4.77 (2H, s), 2.22 (3H, s), 2.08 (3H, s).

Step B

Chlorination and methanolysis of anhydro-2,2′,2″-trichloroethoxycarbonylpenicillin

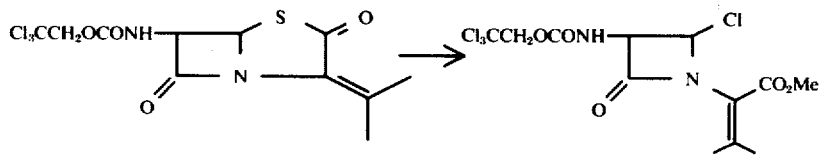

A cold (0°) stirred solution of anhydro-2,2′,2″-trichloroethoxycarbonylpenicillin 1.10 g, 2.95 mmoles), in methylene chloride (40 ml), was treated with a rapid flow of gaseous chlorine for 30 sec. The solvent was then removed to give a foam. This material was redissolved in methylene chloride (25 ml), cooled to 0°, and anhydrous methanol (9.0 ml) was added. After stirring for 0.5 h at 0°, the solvent was removed under reduced pressure and finally under high vacuum to give a white foam. NMR: 6.72 (1H, d, 8.5), 6.12 (1H, d, 4.0), 5.43 (1H, q), 4.82 (2H, s), 3.80 (3H, s), 2.33 (3H, s), 2.06 (3H, s).

Step C

Diallylic bromination of methyl 2-(2′R-chloro-3′S-trichloroethoxycarbonylamino-4′-oxo)azetidinyl-3-methyl-2-butenoate

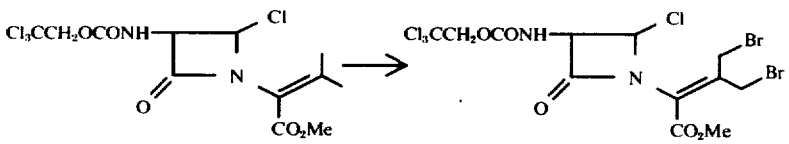

The azetidinone (0.225 g, 0.624 mmole), N-bromosuccinimide (0.249 g, 1.32 mmole) and benzoyl peroxide (4 mg) were heated to reflux in carbon tetrachloride (35 ml) and then irradiated for 0.5 h over a 100 watt Photoflood No. 2 bulb. The reaction mixture was allowed to cool to room temperature, diluted with methylene chloride (100 ml), and washed with ice-cold 5% sodium bisulphite (50 ml), 5% sodium bicarbonate (50 ml) and water (50 ml). Drying and evaporation under reduced pressure afforded a foam (0.232 g). NMR: 6.18 (1H, d, 9), 6.13 (1H, d, 4.0), 5.48 (1H, q), 4.82 (2H, s), 4.9–4.3 (4H, m), 3.90 (3H, s).

Step D

Preparation of methyl 2-(2′R-chloro-3′S-trichloroethoxy carbonylamino-4′-oxo)azetidinyl-3-methyl-3-butenoate Zinc dust (0.155 g, 2.37 mmol) was added in one portion to a cold (0°) stirred solution of the dibromo compound (0.325 g, 0.575 mmol) in acetonitrile-acetic acid (12.5 ml, 4:1 v/v). After vigorous stirring for 3 minutes, the reaction mixture was poured into ice-water (25 ml) and extracted with methylene chloride (75 ml). The organic extract was further washed with cold water (2 × 25 ml), dried (Na₂SO₄) and evaporated under vacuum to give a colorless foam 0.23 g. NMR: 6.30–5.93 (2H, m), 5.43 (1H, q, 9, 4.0), 5.33-4.63 (3H, m), 4.78 (2H, s), 3.80 (3H, s), 1.90 (3H, br s).

Step E

Epoxidation of methyl 2-(2′R-chloro-3′S-trichloroethoxycarbonylamino-4′-oxo)azetidinyl-3-methyl-2-butenoate Peroxytrifluoroacetic acid (7–8 molar equivalents) was added dropwise to a solution of the β,γ-olefin (0.41 g, 1.0 mmol) and dibasic sodium phosphate (0.99 g) in methylene chloride (20 ml) at 0°. The reaction mixture was stirred at 0° for a further 0.75 hr, poured into ice-water (50 ml) and extracted with methylene chloride (75 ml). The organic extract was further washed with ice-water (2 × 25 ml), dried and evaporated under reduced pressure to give a colorless gum, 0.29 g, which is the methyl 2-(2′R-chloro-3′S-trichloroethoxycarbonylamino-4′-oxo)azetidinyl-3-methyl-2-butenoate oxide. NMR: 6.37-5.90 (m, 2H), 5.47 (1H, d of d, J = 9.0 Hz, 4.0 Hz), 4.97–4.70 (1H, m), 4.80 (2H, s), 3.81 (3H, s), 3.03–2.67 (2H, m), 1.52 (3H, s).

Step F

3-Methyl-4-methoxycarbonyl-7S-trichloroethoxycarbonylamino-1-oxa, 5-aza-6S-bicyclo[4,2,0]oct-3en-8-one The mixture of epoxides from Step E was dissolved in pyridine (5 ml) and the solution allowed to stand at room temperature for 6 hr. Isolation as described in Example VII afforded the oxacephem.

EXAMPLE XV

1-Oxadethia-7-amino-desacetoxycephalosporanic acid (oxa-7-ADCA)

Successive treatment of a 70:30 2′S:2′R mixture of benzhydryl 2-(2′-chloro-3′S-trichloroethoxycarbonylamino-4′-oxo)azetidinyl-3-methyl-2-butenoates with (i) N-bromosuccinimide, as described in Example XIV, Step C; (ii) zinc in acetic acid-acetonitrile, as described in Example XIV, Step D; (iii) pertrifluoroacetic acid, as described in Example XIV, Step E; (iv) pyridine, as described in Example VII; (v) zinc in 88% formic acid followed by trifluoroacetic acid, as described in Example VIII, afforded 1-oxadethia-7-ADCA, which is the 3-methyl-4-carboxy-7S-amino-1-oxa, 5-aza-6R-bicyclo[4,2,0]oct-3-en-8-one.

EXAMPLE XVI

Epimerization of benzhydryl 2-(2'R-chloro-3'S-amino-4'-oxo)-azetidinyl-3-methyl-2-butenoate The cis-azetidinone (413 mg, 1.075 mmoles) and tetramethylguanidinium chloride (650 mg, 4.31 mmoles) were refluxed for 12.5 h in redistilled methylene chloride (10 ml). Washing with ice-cold saturated brine, followed by drying and evaporation, afforded a quantitative yield of the 2'R- and 2'S-epimers as a 1:1 mixture. The NMR spectrum benzyhydryl 2-(2'S-chloro-3'S-amino-4'-oxo)azetidinyl-3-methyl-2-butenoate has peaks at 7.29 (10H, s), 6.90 (1H, s), 5.43 (1H, d, 1.4), 4.30 (1H, d, 1.4), 2.30 (3H, s), 2.00 (3H, s).

The equation for the above mentioned reaction is

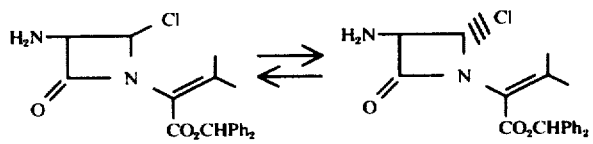

EXAMPLE XVII

Preparation of methyl 2-(2'R-chloro-3'S-phthalimido-4'-oxo)azetidinyl-3-oxo-butanoate

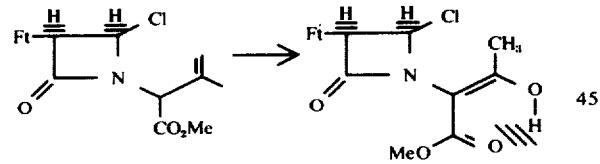

The β,γ-unsaturated ester (135 mg) was dissolved in methylene chloride (15 ml) in a glass vessel fitted with a gas inlet tube and a gas outlet connected to a potassium iodide solution trap. The solution was cooled to −28° C in a dry icecarbon tetrachloride bath, and ozone was passed into the solution until the potassium iodide solution turned red. The reaction mixture was allowed to warm to 0°, and zinc dust (200 mg), water (10 ml) and acetic acid (5 drops) were added. The reaction mixture was shaken for 3 min and the organic layer was separated. The aqueous layer was extracted twice with methylene chloride, and the combined organic layers were washed three times with water, dried, and evaporated. The residue weighed 122 mg (90%), and it crystallized from carbon tetrachloride-petroleum ether, m.p. 156°–158°. NMR: 12.26 (1H, s), 7.86 (4H, m), 6.05 (1H, d, 4Hz), 5.66 (1H, d, 4Hz), 3.83 (3H, s), 2.40 (3H, s).

EXAMPLE XVIII

Preparation of methyl 2-(2'S-chloro-3'S-phthalimido-4'-oxo)azetidinyl-3-oxo-butanoate

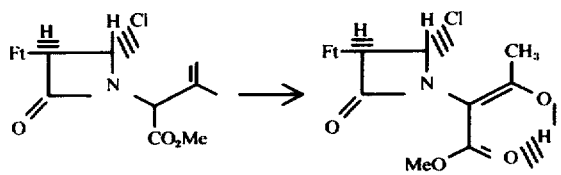

A solution of the β,γ-unsaturated ester (170 mg, 0.47 mmol), in methylene chloride (30 ml), was cooled to −23° C in a dry ice-carbon tetrachloride bath, and ozone was introduced during a period of 1 min, the reaction being monitored by tlc. The cooling bath was then removed and to the resulting solution was added zinc dust (100 mg) and acetic acid (0.5 ml). Stirring was continued at room temperature for 20 min, and the mixture was then filtered and the filtrate washed with ice-cold brine until the aqueous layer was neutral, dried and evaporated to give 170 mg of material which appeared homogeneous by nmr. NMR: 12.53 (1H, s), 7.77 (4H, m), 6.03 (1H, d, 2Hz), 5.30 (1H, d, 2Hz), 3.87 (3H, s), 2.20 (3H, s).

EXAMPLE XIX

Preparation of methyl 2-(2'R-chloro-3'S-trichloroethoxy carbonylamino-4'-oxo)azetidinyl-3-oxo-butanoate

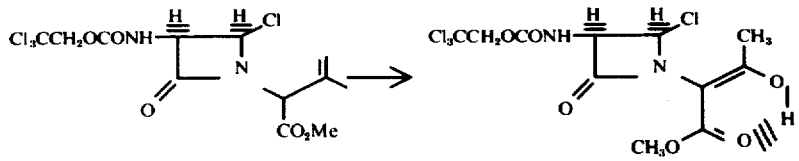

The β,γ-olefin (0.192 g. 0.47 mmol), in methylene chloride (40 ml), was treated with a stream of ozone at −20° C. The reaction mixture was then allowed to warm slowly to 0° and treated successively with ice-water (10 ml), zinc dust (0.11 g) and ten drops of glacial acetic acid. After 0.5 hr at 0°, this mixture was poured onto ice-water (25 ml) and extracted with methylene chloride (2 × 50 ml). The combined organic extracts were dried and evaporated under reduced pressure to give a colorless foam, 0.16 g. NMR: 12.3 (1H, br s), 6.13 (1H, d, 8.5Hz), 5.77 (1H, d, 4.0Hz), 5.40 (1H, d of d), 4.78 (2H, s), 3.81 (3H, s), 2.13 (3H, s).

EXAMPLE XX

Halogenation of methyl 2-(2'R-chloro-3'S-phthalimido-4'oxo)azetidinyl-3-oxo-butanoate

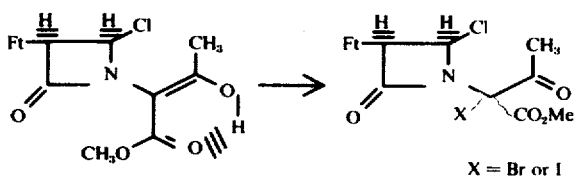

X = Br or I

Pyrrolidone hydrotribromide (186 mg, 0.38 mmol) was added to a solution of the enol (137 mg, 0.38 mmol) in chloroform (10 ml). The mixture was stirred at room temperature for 10 min and then evaporated to dryness under reduced pressure. The residue was triturated with ether, the insoluble solid removed by filtration, and the ether filtrate concentrated to an off-white foam, 164 mg (92%). NMR: 7.86 (4H, m), 6.53 (0.6H, d, 4Hz), 6.33 (0.4H, d, 4Hz), 5.73 (1H, d, 4Hz), 3.96 (3H, br s), 2.73 (1.2H, s), 2.60 (1.8H, s).

The same mixture of epimers which are the methyl 2R and 2S-bromo-2-(2'R-chloro-3'S-phthalimido-4'-oxo)azetidinyl-3-oxobutanoates was obtained following bromination with N-bromosuccinimide in carbon tetrachloride under free radical conditions, or with molecular bromine in carbon tetrachloride.

Iodination of the enol with molecular iodine in the presence of calcium oxide afforded the analogous tertiary iodo compound which is a mixture of the 2R and 2S-iodo-2-(2'R-chloro-3'S-phthalimido-4'-oxo)azetidinyl-3-oxobutanoates.

EXAMPLE XXI

Rearrangement of methyl 2-(2'R-chloro-3'S-phthalimido-4'-oxo)azetidinyl-2-bromo-3-oxo-butanoate

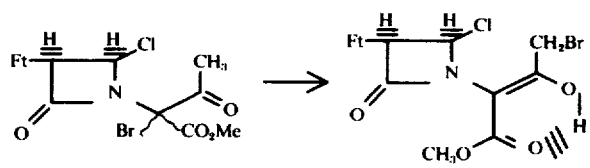

The brominated ketoester (200 mg) was dissolved in benzene (1.5 ml), and a saturated solution of HBr in glacial acetic acid (0.8 ml) was added. The mixture turned orange, and the progress of the reaction was monitored continuously by nmr until the rearrangement was complete (70 hr). The solvent was then removed under reduced pressure. The residue was dissolved in ether and reevaporated. This procedure was repeated three times to give a final material which is the methyl 2-(2'R-chloro-3'S-phthalimido-4'-oxo)azetidinyl-3-oxo-4-bromobutanoate which weighed 192 mg. NMR: 10.66 (1H, br s), 7.80 (4H, m), 6.06 (1H, d, 4Hz), 5.73 (1H, d, 4Hz), 4.43 (2H, q, 11.0Hz), 3.86 (3H, s).

The same compound was obtained following ozonolysis of the mixture of methyl 2R and 2S-2-(2'R-chloro-3'S-phthalimido-4'-oxo)azetidinyl-3-bromomethyl-3-butenoates, prepared in Example XII.

The equation for this reaction is:

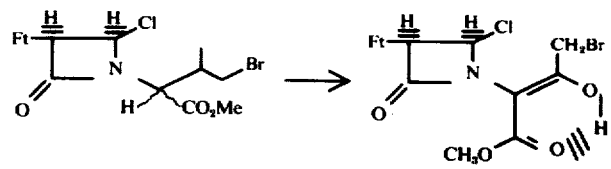

EXAMPLE XXII

Conversion of methyl 2-(2'R-chloro-3'S-phthalimido-4'-oxo)-azetidinyl-3-oxo-4-bromobutanoate into a 1-oxadethia-3-hydroxycephem Step A 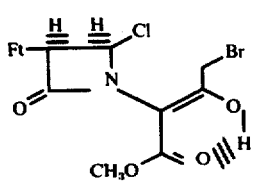 -continued 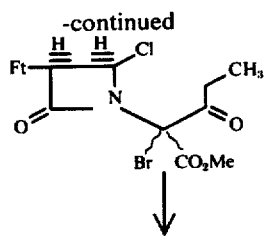

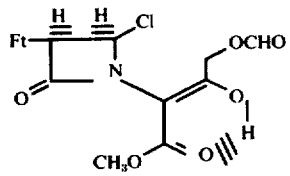

The primary bromide (222 mg, 0.5 mmol) was dissolved in methylene chloride (10 ml) containing tetramethylguanidinium formate (5 molar-equiv). The solution was stirred for 10 hr at room temperature and then washed with water, dried and evaporated to give methyl 2-(2'R-chloro-3'S-phthalimido-4'-oxo)azetidinyl-3-oxo-4-formyloxybutanoate, identified by the presence of a one-proton formyl absorption in the nmr spectrum at 8.15.

Material with the same nmr spectrum was obtained upon reaction of either the tertiary or the primary bromoketone with a solution of sodium formate in anhydrous formic acid.

Step B

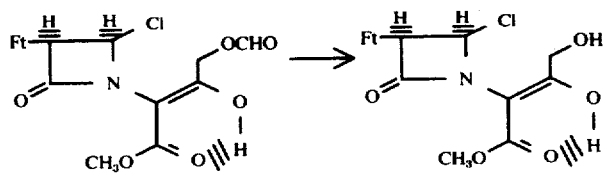

The formate ester (200 mg, 0.49 mmol), in methylene chloride (5 ml), was cooled to 0°, and 4 ml of pre-cooled N anhydrous methanolic HCl was added. The resulting solution was stirred at 0° for 30 min and then poured onto a mixture of brine and ice and extracted with methylene chloride. Drying and evaporation of the methylene chloride layer afforded methyl 2-(2'R-chloro-3'S-phthalimido-4'-oxo)azetidinyl-3-oxo-4-hydroxybutanoate.

Step C

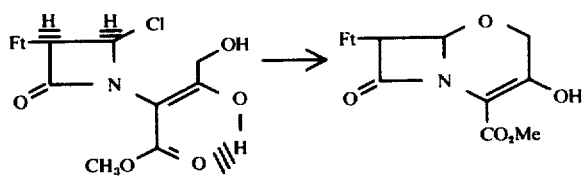

The allylic alcohol (150 mg), and anhydrous stannous chloride (73 mg, 0.40 mmol), were stirred overnight at room temperature in dry dimethoxyethane. Isolation of the product as described in Examples I and II gave the 3-hydroxy-1-oxadethiacephem which the 3-hydroxy-4-methoxycarbonyl-7S-phthalimido-1-oxa,5-aza-6R-bicyclo[4,2,0]oct-3-en-8-one.

EXAMPLE XXIII

Conversion of benzhydryl 2-(2'-chloro-3'S-trichloroethoxycarbonylamino-4'-oxo)azetidinyl-3-oxobutanoate into 1-oxadethia-3-hydroxycephalosporanic acid

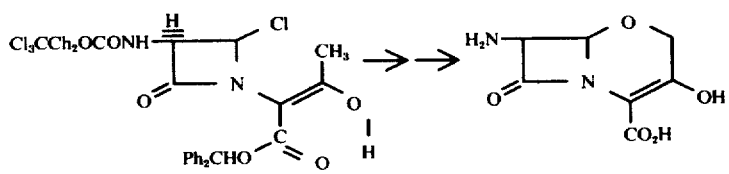

A 70:30 2'S:2'R mixture of enols was brominated with PHT and rearranged to the primary bromoketone, as described in Example XXI. Conversion to the 1-oxadethia-3-hydroxycephem was then performed as described in Example XXII. Removal of the protecting groups in the usual manner afforded the 3-hydroxycephem nucleus which is the 3-hydroxy-4-carboxy-7S-amino-1-oxa,5-aza-6R-bicyclo[4,2,0]oct-3-en-8-one.

I claim:

1. The compound of the formula:

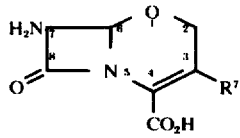

wherein $R^7$ is selected from the group consisting of methyl and hydroxyl.

2. The compound of claim 1, which is the 3-methyl-4-carboxy-7S-amino-1-oxa,5-aza-6R-bicyclo[4,2,0]oct-3-en-8-one.

3. The compound of claim 1, which is the 3-hydroxy-4-carboxy-7S-amino-1-oxa,5-aza-6R-bicyclo[4,2,0]oct-3-en-8-one.

4. The compound of the formula:

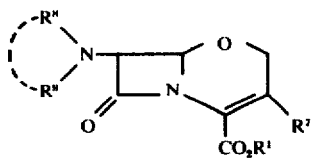

wherein $R^9$ is hydrogen and $R^8$ is hydrogen or

RCOwherein R is selected from the group consisting of

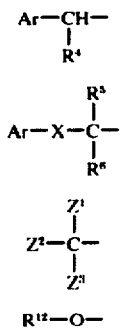

wherein Ar is a monovalent radical selected from the group consisting of

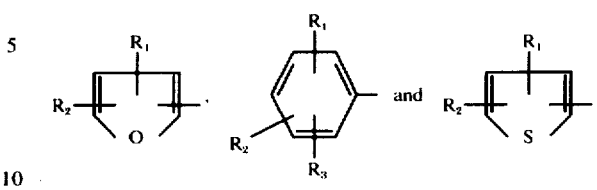

wherein $R_1$, $R_2$ and $R_3$ are each a member selected from the group consisting of hydrogen, chloro, bromo, iodo, trifluoromethyl, phenyl, loweralkyl and loweralkoxy, but only one of said $R_1$, $R_2$ and $R_3$ may represent phenyl;

$R^4$ is hydrogen, amino, carbobenzoxyamino, phenyl, fluoro, chloro, bromo, iodo, carboxyl, $SO_3H$, azido, hydroxy, loweralkanoyloxy or loweralkoxy;

X is oxygen or sulfur;

$R^5$ and $R^6$ are hydrogen, phenyl, benzyl, phenethyl or loweralkyl;

$Z^1$, $Z^2$ and $Z^3$ are loweralkyl or the Ar- group;

$R^{12}$ is 2,2,2-trichloroethyl or benzyl;

provided that when $R^8$ and $R^9$ are taken together with the nitrogen to which they are attached, they form a phthalimido moiety;

$R^7$ is methyl or hydroxy; and $R^1$ is hydrogen, loweralkyl, benzyl, benzhydryl, loweralkoxyloweralkyl, loweralkoxybenzyl, phenacyl, trimethylsilyl, 2,2,2-trichlorethyl, or pivaloyloxy.

5. The compound of claim 4, which is the 3-methyl-4-methoxycarbonyl-7S-phthalimido-1-oxa,5-aza-6R-bicyclo[4,2,0]-oct-3-en-8-one.

6. The compound of claim 4, which is the 3-hydroxy-4-methoxycarbonyl-7S-phthalimido-1-oxa,5-aza-6R-bicyclo[4,2,0]-oct-3-en-8-one.

7. The compound of claim 4, which is the 3-methyl-4-benzhydryloxycarbonyl-7S-phthalimido-1-oxa,5-aza-6R-bicyclo[4,2,0]oct-3-en-8-one.

8. The compound of claim 4, which is the 3-methyl-4-benzhydryloxycarbonyl-7S-trichloroethoxycarbonylamino-1-oxa,5-aza-6R-bicyclo[4,2,0]oct-3-en-8-one.

9. The compound of claim 4, which is the 3-hydroxy-4-benzhydryloxycarbonyl-7S-trichloroethoxycarbonylamino-1-oxa,5-aza-6R-bicyclo[4,2,0]oct-3-en-8-one.

* * * * *